United States Patent [19]
Buck et al.

[11] Patent Number: 5,344,385
[45] Date of Patent: Sep. 6, 1994

[54] STEP-DOWN SKELETAL MUSCLE ENERGY CONVERSION SYSTEM

[75] Inventors: Keith E. Buck, Alamo; David J. Farrar, Richmond; Robert J. Harvey, Stanford; Philip Litwak, Novato; John R. Rueff, Concord, all of Calif.

[73] Assignee: Thoratec Laboratories Corporation, Berkeley, Calif.

[21] Appl. No.: 767,789

[22] Filed: Sep. 30, 1991

[51] Int. Cl.$^5$ ............................................. A61N 1/362
[52] U.S. Cl. ......................................... 600/16; 623/3
[58] Field of Search ........................ 623/3; 600/16–18

[56] References Cited

U.S. PATENT DOCUMENTS

| | | |
|---|---|---|
| 3,518,702 | 7/1970 | La Russa . |
| 3,878,839 | 4/1975 | Norton et al. . |
| 3,919,722 | 11/1975 | Harmison . |
| 4,004,299 | 1/1977 | Runge . |
| 4,023,468 | 5/1977 | Poirier . |
| 4,047,849 | 9/1977 | Clay . |
| 4,101,984 | 7/1978 | MacGregor . |
| 4,104,005 | 8/1978 | Poirier . |
| 4,133,616 | 1/1979 | Poirier . |
| 4,143,425 | 3/1979 | Runge . |
| 4,152,786 | 5/1979 | Clark et al. . |
| 4,167,046 | 9/1979 | Portner et al. . |
| 4,173,796 | 11/1979 | Jarvik . |
| 4,176,411 | 12/1979 | Runge . |
| 4,195,623 | 4/1980 | Zeff et al. . |
| 4,222,127 | 9/1980 | Donachy et al. . |
| 4,230,096 | 10/1980 | Zeff et al. . |
| 4,231,354 | 11/1980 | Kurtz et al. . |
| 4,240,409 | 12/1980 | Robinson . |
| 4,302,854 | 12/1981 | Runge . |
| 4,369,530 | 1/1983 | Robinson et al. . |
| 4,374,669 | 2/1983 | Mac Gregor . |
| 4,376,312 | 3/1983 | Robinson . |
| 4,381,567 | 5/1983 | Robinson et al. . |
| 4,384,829 | 5/1983 | Conley et al. . |
| 4,389,737 | 6/1983 | Robinson et al. . |
| 4,397,049 | 8/1983 | Robinson et al. . |
| 4,411,268 | 10/1983 | Cox . |
| 4,430,998 | 2/1984 | Harvey et al. . |
| 4,453,537 | 6/1984 | Spitzer . |
| 4,457,673 | 7/1984 | Conley et al. . |
| 4,493,314 | 1/1985 | Edwards, II . |
| 4,512,726 | 4/1985 | Strimling . |
| 4,547,911 | 10/1985 | Strimling . |
| 4,573,997 | 3/1986 | Wisman et al. . |
| 4,581,029 | 4/1986 | Joh . |
| 4,583,523 | 4/1986 | Kleinke et al. . |
| 4,600,405 | 7/1986 | Zibelin . |
| 4,623,350 | 11/1986 | Lapeyre et al. . |
| 4,627,836 | 12/1986 | Mac Gregor . |
| 4,652,265 | 3/1987 | McDougall . |
| 4,662,358 | 5/1987 | Farrar et al. . |
| 4,665,896 | 5/1987 | LaForge et al. . |
| 4,666,443 | 5/1987 | Portner . |
| 4,675,361 | 6/1987 | Ward, Jr. . |
| 4,685,446 | 8/1987 | Choy . |
| 4,688,998 | 8/1987 | Olsen et al. . |
| 4,689,383 | 8/1987 | Riffle et al. . |
| 4,690,134 | 9/1987 | Snyders . |
| 4,756,302 | 7/1988 | Portner et al. . |
| 4,759,760 | 7/1988 | Snapp, Jr. . |
| 4,769,031 | 9/1988 | McGough et al. . |
| 4,771,765 | 9/1988 | Choy et al. . |
| 4,782,817 | 11/1988 | Singh et al. . |

(List continued on next page.)

OTHER PUBLICATIONS

Farrar, et al.; J. of Heart and Lung Transplantation, vol. 11, No. 5, 1992, pp. S341–S350.

(List continued on next page.)

Primary Examiner—William E. Kamm
Assistant Examiner—J. P. Lacyk
Attorney, Agent, or Firm—Baker & Botts

[57] ABSTRACT

This invention provides a simple skeletal muscle linear pull energy convertor which can harness the maximal amount of muscle power for a wide variety of implantable medical devices, including the full range of circulatory support devices. The muscle powered system provides completely implantable circulatory support as an alternative to cardiac transplantation, with a quality of life relatively free from external batteries, transcutaneous energy transmission and other electromechanical hardware.

25 Claims, 29 Drawing Sheets

U.S. PATENT DOCUMENTS

| | | |
|---|---|---|
| 4,813,952 | 3/1989 | Khalafalla . |
| 4,822,357 | 4/1989 | Forster et al. . |
| 4,826,477 | 5/1989 | Adams . |
| 4,838,281 | 6/1989 | Rogers et al. . |
| 4,838,889 | 6/1989 | Kolff . |
| 4,846,831 | 7/1989 | Skillin . |
| 4,846,856 | 7/1989 | Burger et al. . |
| 4,895,150 | 1/1990 | Isaacson et al. . |
| 4,908,012 | 3/1990 | Moise et al. . |
| 4,919,661 | 4/1990 | Gibney . |
| 4,925,443 | 5/1990 | Heilman et al. . |
| 4,936,317 | 6/1990 | MacGregor . |
| 4,944,748 | 7/1990 | Bramm et al. . |
| 4,955,856 | 9/1990 | Phillips . |
| 4,957,504 | 9/1990 | Chardack . |
| 4,969,864 | 11/1990 | Schwarzmann et al. . |
| 4,979,936 | 12/1990 | Stephenson et al. . |
| 4,985,014 | 1/1991 | Orejola . |
| 4,994,078 | 2/1991 | Jarvik . |
| 4,995,857 | 2/1991 | Arnold . |
| 4,997,431 | 3/1991 | Isner et al. . |
| 5,006,104 | 4/1991 | Smith et al. . |
| 5,007,927 | 4/1991 | Badylak et al. . |
| 5,011,380 | 4/1991 | Kovacs . |
| 5,040,944 | 8/1991 | Cook . |

OTHER PUBLICATIONS

Farrar, et al.; ASAIO, 1992 Abstracts, p. 35.
Acker, et al.; in Chiu, Biomedical Cardiac Assist, 1986, Ch. 2, pp. 19–28.
Acker, et al.; J. Thorac Cardiovasc Surg, vol. 92, No. 4, 1986, pp. 733–746.
Acker, et al.; J. Applied Physiology, vol. 62, No. 3, 1987, pp. 1264–1270.
Acker, et al.; Science, vol. 236, 1987, pp. 324–327.
Acker, et al.; J. Thorac Cardiovasc Surg, vol. 94, No. 2, 1987, pp. 163–174.
Acker, et al.; J. Thorac Cardiovasc Surg, vol. 94, No. 5, 1987, pp. 702–709.
Anderson, et al.; PACE, vol. 11, No. 11, 1988, pp. 2128–2134.
Armenti, et al.; ACS Surgical Forum, vol. XXXV, pp. 258–260.
Badylak, et al.; Medical & Biological Engineering & Computing, vol. 27, No. 2, 1989, pp. 159–162.
Baller, et al.; J. Physiol, vol. 150, No. 2, 1960, pp. 417–439.
Bartlett, et al.; Plastic and Reconstructive Surgery, vol. 67, No. 5, 1981, pp. 631–636.
Barnett, et al.; American J. Physiol., vol. 239, No. 1, 1980, C39–C46.
Bitto, et al.; Pediatric Cardiology, Proceedings of the Second World Congress, Springer-Verlag, pp. 609–612.
Bitto, et al.; Progress in Artificial Organs–1985, ISAO Press, pp. 441–446.
Brister, et al.; Canadian J. of Surgery, vol. 28, No. 4, 1985, pp. 341–344.
Brown, M. D., et al.; Pflugers Arch., vol. 361, No. 3, 1976, pp. 241–250.
Carlson, et al.; Muscle Physiology, Prentice-Hall, 1974, Ch. 2, pp. 26–51.
Carpenter, et al.; The Lancet, No. 8440, Jun. 1, 1985, p. 1267, (Letter to Editor).
Chachques, et al.; Progress in Artificial Organs–1985, ISAO Press, pp. 409–440.
Chachques, et al.; European Surgical Research, 21th Congress, 1986, pp. 89–90 (Abstract 160).
Chachques, et al.; Life Support Systems, vol. 5, No. 4, 1987, pp. 323–327.
Chachques, et al.; Annals of the New York Academy of Sciences, vol. 494, 1987, pp. 445–448.
Chachques, et al.; The International Journal of Artificial Organs, vol. 11, No. 6, 1988, pp. 469–474.
Chachques, et al.; An Thorac Surg, vol. 47, No. 4, 1989, pp. 600–604.
Chachques, et al.; J. of Heart Transplantation, vol. 9, No. 3, Pt. 1, 1990, pp. 239–251.
Ugolini, in CHIU; Biomechanical Cardiac Assist, 1986, Ch. 14, pp. 193–210.
Chiu, et al.; J. Cardiac Surg, vol. 1, No. 4, 1986, pp. 385–392.
Chiu, et al.; J. Thorac Cardiovasc Surg, vol. 94, No. 5, 1987, pp. 694–701.
Christ, et al.; Annals of Plastic Surgery, vol. 8, No. 2, 1982, pp. 118–121.
Clark, et al.; American J. Physiol., vol. 254, No. 2, Pt. 1, 1988, pp. C258–C266.
Dahm, et al.; DMW, vol. 113, No. 15, 1988, pp. 610–613 (German).
Dewar, et al.; J. Thorac Cardiovasc Surg, vol. 87, No. 3, 1984, pp. 325–331.
Dewar, et al.; Ann Thorac Surg, vol. 44, No. 6, 1987, pp. 618–624.

OTHER PUBLICATIONS

Drinkwater, et al.; Surgical Forum, vol. XXXI, 1980, pp. 270–274.
Eisenberg, et al.; Cell Tissue Res, vol. 220, No. 3, 1981, pp. 449–471.
Farrar, et al.; IEEE Engineering in Medicine and Biology Magazine, vol. 5, No. 1, 1986, pp. 19–25.
Farrar, et al.; J. Thorac Cardiovasc Surg, vol. 95, No. 2, 1988, pp. 191–200.
Farrar, et al.; New England Journal of Medicine, vol. 318, No. 6, 1988, pp. 333–340.
Farrar, et al.; Journal of Heart Transplantation, vol. 9, No. 4, 1990, pp. 415–423.
Frey, et al.; Eur. Surg. Res., vol. 16, No. 4, 1984, pp. 232–237.
Ganzel, et al.; Ann Thorac Surg, vol. 47, No. 1, 1989, pp. 113–120.
Geddes, et al.; PACE, vol. 13, No. 6, 1990, pp. 783–795.
Geddes, et al.; Trans Am Soc Artif Intern Organs, vol. XXXVII, 1991, pp. 19–23.
Ginzton, et al.; Circulation, vol. 80, No. 4, 1989, pp. 816–822.
Glenn, et al.; The Annals of Thoracic Surgery, vol. 30, No. 2, 1980, pp. 106–109.
Hammond, et al.; Journal of Heart Transplantation, vol. 9, No. 3, Pt. 1, 1990, pp. 252–257.
Hudlicka, et al.; Pflugers Arch, vol. 369, No. 2, 1977, pp. 141–149.
Hume; Transactions of the Southern Surgical Assoc, vol. LXXIX, 1967, pp. 200–202.
Kantrowitz, et al.; Surgical Forum, vol. IX, 1959, pp. 266–268.
Kantrowitz, et al.; Trans. Amer. Soc. Artif. Int. Organs, vol. VI, 1960, pp. 305–310.
Kochamba, et al.; Trans. ASAIO, vol. 33, No. 3, 1987, pp. 404–407.
Kochamba, et al.; Ann Thorac Surg, vol. 45, No. 6, 1988, pp. 620–625.
Kusaba, et al.; Trans. Amer. Soc. Artif. Int. Organs, vol. XIX, 1973, pp. 251–257.
Kusserow, et al.; Trans. Amer. Soc. Artif. Int. Organs, vol. X, 1964, pp. 74–78.
Li, et al.; ASAIO, vol. 36, 1990, pp. M382–M386.
Macoviak, et al.; Surgery, vol. 90, No. 2, 1981, pp. 271–277.
Macoviak, et al.; J. Thorac Cardiovasc Surg, vol. 81, No. 4, 1981, pp. 519–527.
Macoviak, et al.; J. Surgical Research, vol. 32, No. 5, 1982, pp. 429–439.
Magovern, et al.; Ann Thorac Surg, vol. 41, No. 1, 1986, p. 116 (Correspondence to Editor).
Magovern, et al.; Ann Thorac Surg, vol. 44, No. 4, 1987, pp. 379–388.
Magovern, et al.; Ann Thorac Surg, vol. 45, No. 6, 1988, pp. 614–619.
Magovern, et al.; J Heart Transplantation, vol. 9, No. 3, Pt. 1, 1990, pp. 258–263.
Mannion, et al.; Surgical Clinics of North America, vol. 65, No. 3, 1985, pp. 679–687.
Mannion, et al.; Circulation Research, vol. 58, No. 2, 1986, pp. 298–304.
Mannion, et al.; J Thorac Cardiovasc Surg, vol. 91, No. 4, 1986, pp. 534–544.
Mannion, et al.; Trans. ASAIO, vol. 32, No. 1, 1986, pp. 454–460.
Mannion, et al.; Surgical Forum, vol. XXXVII, 1986, pp. 211–213.
Mannion, et al.; Circulation, vol. 76, No. 1, 1987, pp. 155–162.
Molteni, et al.; J Thorac Cardiovasc Surg, vol. 97, No. 3, 1989, pp. 439–446 (Case Report).
Moreira, et al.; J Cardiac Surgery, vol. 4, No. 2, 1989, pp. 164–179.
Nakamura, et al.; J Surgical Research, vol. IV, No. 10, 1964, pp. 435–439 (Experimental Study).
Neilson, et al.; Heart Transplantation, vol. IV, No. 3, 1985, pp. 343–347.
Novoa, et al.; Trans Am Soc Artif Intern Organs, vol. XXXV, 1989, pp. 408–411.
Oaks, et al.; Trans Am Soc Artif Inern Organs, vol. 33, No. 3, 1987, pp. 408–412.
Oda, et al.; J Surgical Research, vol. 30, No. 2, 1981, 142–153 (Experimental Study).
O'Rourke, et al.; British Heart Journal, vol. 41, No. 3, 1979, pp. 308–316.
Pattison, et al.; Supplement II Circulation, vol. 80, No. 4, 1989, pp. II-670 (Abstract 2663).
Pennington, et al.; J Thorac Cardiovasc Surg, vol. 96, No. 6, 1988, pp. 901–911.
Petrofsky, et al.; Med. & Biol. Eng. & Comput., vol. 17, No. 5, 1979, pp. 583–592.

OTHER PUBLICATIONS

Pette; Medicine and Science in Sports & Exercise, vol. 16, No. 6, 1984, pp. 517–528.
Pette, et al.; Pflugers Arch, vol. 364, No. 2, 1976, pp. 103–112.
Pluskal, et al.; Biochemical and Biophysical Research Communications, vol. 113, No. 1, 1983, pp. 325–331.
Ramsey; in Bourne, The Structure and Function of Muscle, vol. II, Academic Press, 1960, Ch. VI, pp. 303–358.
Raymond; JAMA, vol. 255, No. 15, 1986, pp. 1977–1979.
Roy, et al.; Biochemical and Biophysical Research Communications, vol. 89, No. 1, 1979, pp. 181–187.
Sakakibara, et al.; M375. ASAIO, vol. 36, No. 3, 1990, pp. M372–375.
Salmons; in Pette, Plasticity of Muscle, Walter de Gruyter, 1979, pp. 387–399.
Salmons, et al.; NATURE, vol. 263, No. 5572, 1976, pp. 30–34.
Salmons, et al.; Muscle & Nerve, vol. 4, No. 2, 1981, pp. 94–105.
Schottstaedt, et al.; J Bone and Joint Surgery, vol. 37-A, No. 5, 1955, pp. 897–919.
Shepherd, et al.; Brit. J. Surg., vol. 55, No. 1, 1968, pp. 91–92.
Silberner; Science News, vol. 129, No. 18, 1986, pp. 284–285.
Sola, et al.; Experimental Neurology, vol. 41, No. 4, 1973, pp. 76–100.
Sola, et al.; Circulation, vol. 71, No. 2, 1985, pp. 341–348 (Laboratory Investigation).
Sola, et al.; J Heart Transplantation, vol. 9, No. 2, 1990, pp. 151–159.
Sreter, et al.; Experimental Neurology, vol. 75, No. 1, 1982, pp. 95–102.
Spotnitz, et al.; Trans. Amer. Soc. Artif. Int. Organs, vol. XX-B, 1974, pp. 747–756.
Stevens, et al.; J Surgical Research, vol. 46, No. 1, 1989, pp. 84–89.
Tacker, et al.; J Cardiac Surgery Supplement, vol. 6, No. 1, 1991, pp. 245–251.
Thoma, et al.; Artificial Organs Supplement, vol. 5, 1981, pp. 441–445.
Vachon, et al.; Medical & Biological Engineering, vol. 13, No. 2, 1975, pp. 252–260.
Von Recum, et al.; J Surgical Research, vol. 23, No. 6, 1977, pp. 422–427.
Walsh, et al.; Eighth Annual Conference of the IEEE Engineering in Medicine and Biology Society, vol. 1, 1986, pp. 62–64.
Walsh, et al.; Surgical Forum, vol. XXXVII, 1986, pp. 205–207.
Zancolli, et al.; J. Bone and Joint Surgery, vol. 55-A, No. 6, 1973, pp. 1265–1275.
G. H. Bourne; *The Structure and Function of Muscle*, vol. I, 38 (*Academic Press*, 1972).
Bridges et al., *Circulation*, 80 (suppl. III): III 183–III 191 (1989).
Schwartz et al; *Principles of Surgery*, Ch. 46 (Plastic and Reconstructive Surgery) 2093–2097 (5th ed. 1989).

STEP-DOWN SKELETAL MUSCLE ENERGY CONVERSION SYSTEM

BACKGROUND OF THE INVENTION

The present invention relates to an implantable energy conversion system utilizing skeletal muscle power to operate an implanted device and, in particular, to a system for converting the linear contractile force of a muscle into sufficient power for operating of a circulatory support device.

Due to the dramatic increase in successful heart transplantations in recent years, today's heart disease patients more readily elect to undergo this procedure and generally expect that a donor heart will be available when required. Yet, the data shows that 88% to possibly as high as 96% of those that need a donor heart will not receive one due to the very limited number available (2,000 per year against a need of 17,000 to 50,000 per year in the United States alone). Those patients awaiting heart transplantation demonstrate the clear but unfulfilled need for a chronic artificial heart device as an alternative to heart transplantation. A system is needed to provide a therapeutic alternative to cardiac transplantation which, because of the limited supply of donor hearts, can only meet the needs of a fraction of the patients who could benefit annually from cardiac replacement or assistance. Thus, some form of chronic circulatory support is needed if large groups of patients with Congestive Heart Failure ("CHF") are to have the opportunity to live out a near-normal life span with a reasonable quality of life.

Attempts have been made to meet this need by developing externally powered mechanical artificial hearts. In December 1981, a Symbion artificial heart was implanted in Barney Clark in an orthotopic position with the natural heart excised. That same year, Thoratec Laboratories Corporation was preparing the Pierce-Donachy design Ventricular Assist Device (VAD) for clinical trials as a VAD in the left ventricle, right ventricle, or both positions, thus serving as a heterotopic artificial heart with the natural heart left in place. In April 1982, the first clinical case with the Thoratec TM VAD System was implanted. The clinical work over the past eight years has shown that patients do quite well when adequate circulation of the blood is restored and maintained before the onset or irreversible cardiogenic shock.

Pneumatic systems require that the patient be tethered to a bulky, external console which powers and controls the pneumatic system. The National Heart Lung and Blood Institute (NHLBI) has been supporting the development of electrically powered totally implantable artificial hearts and left ventricular assist systems and clinical trials are soon to begin with one such system. At present, the major limitation of the clinical work with circulatory support devices is the need for simple, reliable implantable power sources for driving the blood pumps, and thus allowing the patients to be discharged from the hospital in order to resume a near normal life. Electromechanical systems have the disadvantage of requiring bulky hardware for external power, transcutaneous electrical power transmission systems, implantable batteries and other components.

The use of skeletal muscle power provides a new opportunity for realizing completely implantable tether-free mechanical circulatory support, free from any external power sources such as batteries. Skeletal muscle powered circulatory support systems have the potential of providing a simpler alternative to electromechanical systems, and of offering an improved quality of life for the patient by eliminating the need for electricity (except for the low power requirements of muscle stimulation). All of the associated external and implanted power conditioning hardware, batteries, coils, and the like could be eliminated and replaced by natural muscle biochemical and biophysical processes.

The key problem with skeletal muscle as a power source is how to harness the available energy and utilize it efficiently for maximal circulatory support. Experimental work focused primarily on the physiology of skeletal muscle while it was being conditioned (or transformed) from predominantly fast-twitch muscle fibers, susceptible to fatigue into muscle bundles with predominately slow-twitch muscle fibers capable of chronic periodic contractions. As it was established that such transformed skeletal muscle was capable of long-term stimulation-contraction, surgeons began clinical applications. In one application, called dynamic cardiomyoplasty, the distal end of the latissimus dorsi muscle was carefully dissected from its natural anatomical position across the lateral posterior area of the back and moved into the thoracic cavity, where it was then wrapped around the heart. After a three to four week healing period, stimulation of the transformed latissimus dorsi was initiated. As it contracted, the coiled muscle shortened, thus causing it to squeeze the epicardial surfaces of the heart. When timed properly in synchrony with the heart, this action was meant to cause an augmentation of the pumping function of the heart. Clinical experience to date on dynamic cardiomyoplasty, where the latissimus dorsi is wrapped around the heart, has demonstrated (with patient follow-up out to several years) that a chronically stimulated fatigue-resistant skeletal muscle as a long term power source is quire feasible. However, there is considerable controversy over the actual amount of assistance and patient benefit provided with this technique.

To obtain more cardiac assistance other investigators have proposed using muscles such as the latissimus dorsi or rectus abdominis to form a blood pump independent and distinct from the heart. In 1960, Kantrowitz demonstrated diastolic counterpulsation obtained with a diaphragm muscle wrapped around the distal thoracic aorta (Kantrowitz, *Trans. ASAIO*, 6:305, 1960). In 1964, Kusserow demonstrated actuation of a pump by direct linear contraction of a muscle. The quadriceps muscle of a dog was mobilized and attached to the handle of an external pump; the pump could be operated for up to 8 hours by electric stimulation of the muscle. (Kusserow, et al. (1964) Trans. ASAIO, 10:74). However, methods for internalizing a pump relying on linear contraction of a muscle have not been developed in the art. Rather, developments have been based on compression by transformed skeletal muscle. These developments include aortic counterpulsation devices with a muscle wrapped around a pouch connected to the aorta (Acker, et al., 1987, *J. Thoracic Cardiovasc. Surg.*, 94:163–174, U.S. Pat. No. 5,007,927), and a dual-chamber system with the muscle wrapped around one chamber coupled to a blood pump chamber used for counterpulsation (U.S. Pat. No. 4,979,936). Apical-to-aortic valved conduits, similar in placement to today's ventricular assist devices, have also been fabricated with muscles wrapped around the pumping chamber (U.S. Pat.

Nos. 4,813,952 and 4,759,760). Most of these approaches have demonstrated inadequate power available for left ventricular assistance and as a result, a number of groups have suggested that skeletal muscle ventricles might be more appropriate for right heart assist (Bridges, et al., 1989, *Circulation,* 80 (supp. III): III 183-III 191) Sakakibara, et al., 1990, *Trans. ASAIO,* 36:M372-M375, Li, et al., 1990, *Trans. ASAIO,* 36:M382-386).

The power obtained from using the muscle in any of the wrap-around configurations, either for blood pump actuation or for direct wrapping around the heart is greatly inefficient, and perhaps physiological damaging to the muscle. Skeletal muscle is accustomed to pulling in direct tension when it contracts, and the force is dependent on the preload stretch. When the latissimus dorsi is wrapped around the heart or around a blood pump, there is an inefficient pre-stretch of the muscle, and there is also nothing for the muscle to pull against. Muscle capillary blood flow is also impaired during contraction, and mechanisms might be needed to limit preload impairment of muscle blood flow, such as with a solenoid valve which limits the time of filing (Geddes, et al., *PACE,* 13:783-795, 1990). The net effect with any of these approaches is very poor pumping mechanics with barely sufficient power to augment the circulation. Others have attempted to leave the latissimus dorsi in situ, and have it squeeze a pouch between the muscle and the rib cage (U.S. Pat. Nos. 4,453,537 and 4,771,765), but this has also proven to be an inefficient method of pumping (Chiu, et al., 1987, *J. Thoracic Cardiovasc. Surg.,* 94:694-701, Novoa, et al., 1989, *Trans. ASAIO,* 35:408-411).

A strong need therefore exists for a system which can maximally utilize skeletal muscle power for a full range of circulatory support needs.

SUMMARY OF THE INVENTION

It is an object of the present invention to provide a skeletal muscle powered energy convertor/actuator for operating an implanted device and, in particular, for operating an implanted medical circulatory support device.

It is another object of the present invention to harness the maximum available energy of a skeletal muscle as part of a chronic implanted system and to thereby provide a quality of life free of transcutaneous power transmissions external batteries and other electrical power conditioning hardware.

A further object of the invention is to provide a high pressure-low volume hydraulic convertor/actuator which converts the linear contractile force of a muscle into high pressure hydraulic power for operating an implanted medical device.

A still further object of the invention is to provide a two-stage hydraulic actuator for transforming high pressure hydraulic power into physiological pressure power capable of powering a variety of low pressure circulatory support devices.

Another object of the invention is to provide a means for attaching the muscle to the actuator so as to promote quick healing and a secure junction therebetween.

Yet another object of the present invention is to provide an access port to the hydraulic actuator thereby enabling connection to an extracorporeal power source when muscle energy is not utilized, and also allowing for adjustment of the muscle pre-stretch through adjustment of the hydraulic fluid contained therein.

These and other objects are achieved by the present invention, which provides an implantable skeletal muscle energy conversion system including an energy convertor connected to the detached end of a skeletal muscle which converts the energy of linear muscle contraction into energy usable by an implantable medical device and a means for stimulating the muscle to contract.

In a preferred embodiment, or the present invention provides a muscle stimulator, a mechanical to hydraulic energy convertor, biologic attachments (rib fixation and muscle/tendon attachment), optionally a two-stage hydraulic actuator, and an implanted medical device powered therefrom. Operation of the present invention includes removing one end of a skeletal muscle, preferably the latissimus dorsi, and reattaching it to an energy converter that has been securely affixed to the ribs. A muscle stimulator activates the skeletal muscle which then contracts in direct linear tension. In a preferred mode, an energy convertor converts mechanical force in direct tension to high pressure hydraulic energy (preferably from about 80-200 psi). The output of the energy convertor is connected to a two stage hydraulic actuator which transforms the high pressure hydraulic power into physiological pressure power and thereby drives an implanted medical device, such as a blood pump.

The invention also includes a dual access port which is inserted in a high pressure hydraulic transmission line interconnecting the hydraulic convertor and hydraulic actuator of the preferred embodiment, although use of the dual access port is not restricted to the skeletal muscle energy conversion system described herein. This port is ideally utilized during the implantation and early post-operative period of circulatory support devices, and more specifically, those support devices which are powered by skeletal muscle. The dual access port permits actuation of a circulatory support device immediately after implantation, giving the skeletal muscle time to be conditioned, and further permits monitoring of the implanted hydraulic actuator in order to assess the capabilities of the skeletal muscle power.

The invention further includes a method of attaching skeletal muscle to the skeletal muscle energy conversion system so as to ensure quick healing and a secure junction therebetween.

The skeletal muscle energy conversion system of the present invention is a universal energy source which can power a wide variety of implanted medical devices, including circulatory support blood pumps ranging from intra-aortic balloons to total artificial hearts.

BRIEF DESCRIPTION OF THE DRAWINGS

The novel features of the invention are set out with particularity in the appended claims, but the invention will be understood more fully and clearly from the following detailed description of the invention as set forth in the accompanying drawings, in which:

FIG. 28 is a perspective view of the access port shown in

FIG. 27 in a second position;

DETAILED DESCRIPTION OF THE PREFERRED EMBODIMENTS

Figure 1:
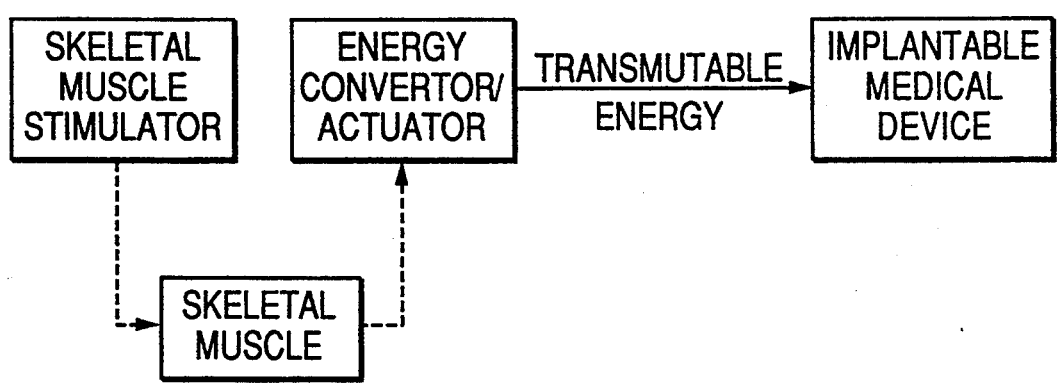
FIG. 1 is a flow chart schematic of the skeletal muscle energy conversion system of the present invention.

In order to harness the maximum amount of energy from a skeletal muscle, this invention provides an implantable skeletal muscle energy convertor/actuator which converts energy expended in linear contraction of a muscle into transmutable energy that may be used to drive an implanted medical device. The form of the usable energy may be hydraulic, pneumatic or electrical. As schemtically illustrated in FIG. 1, the energy convertor/actuator is coupled to an implanted medical device by a means appropriate for the transmission of energy from the convertor/actuator to the implanted medical device. Representative medical devices, which may be operated by the transmissable, usable energy, include circulatory support devices such as intra-aortic balloons, ventricular assist devices, intraventricular balloons, artificial ventricles and artificial hearts, pneumatic or hydraulic powered prostheses, and pumps for chronic drug delivery, such as insulin pumps, and the like.

Operability of Muscle-Powered System

According to the present invention, skeletal muscle contraction in a linear actuation scheme achieves the necessary power for operating a variety of implanted medical devices, such as circulatory support devices including counterpulsation blood pumps and prosthetic ventricles. By leaving a skeletal muscle substantially in place, and just disconnecting one end, the muscle can contract in a normal manner with an intact blood supply and innervation. Thus, all of the muscle fibers and segments can contribute to the force generated in the manner of a normal contraction.

Figure 2:
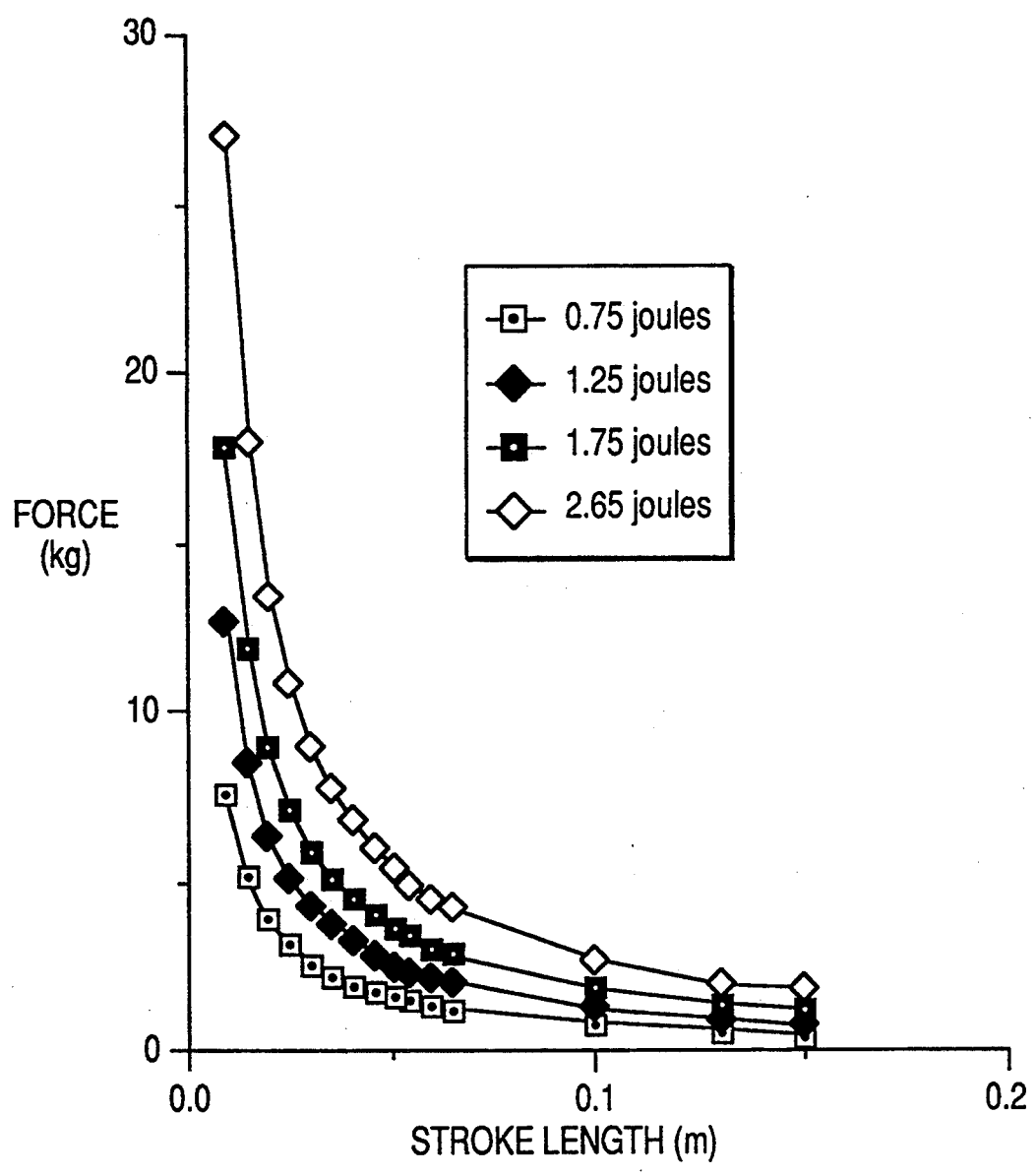
FIG. 2 is a graphical representation of muscle force versus stroke length for various energy levels.

Mechanical work from the muscle is obtained in the form of a force acting over a distance. FIG. 2 illustrates the relationship between muscle forces and stroke lengths required to produce the stroke work necessary for a range of implanted medical devices, such as counterpulsation blood pumps or prosthetic ventricles.

Figure 3:
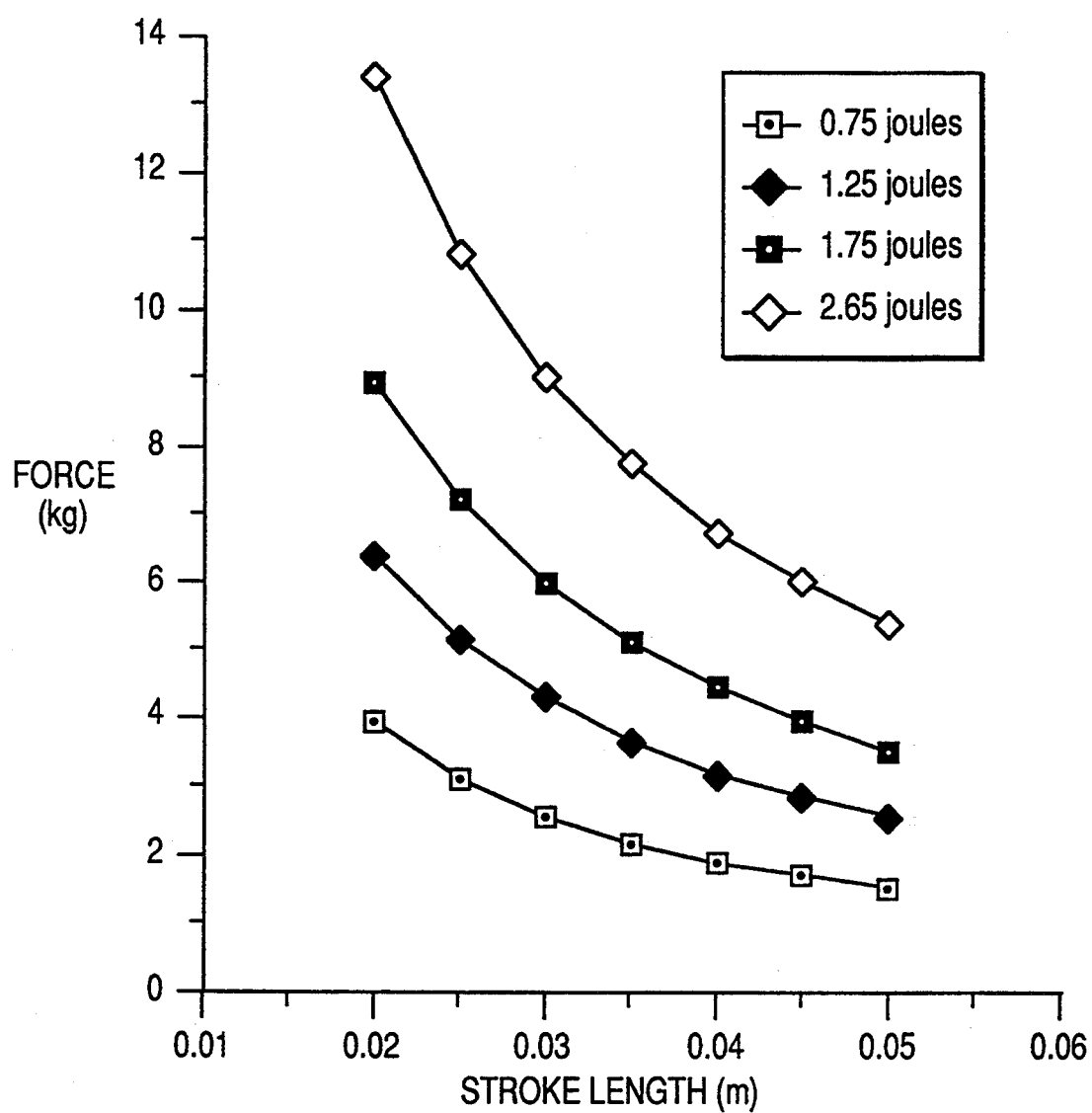
FIG. 3 is an enlargement of a portion of the graph shown in FIG. 2.

The stroke should be as short as possible in order to minimize problems due to encapsulation and fibrous ingrowth, which could affect performance of chronic devices. However, as the stroke gets shorter, the force that must be exerted increases. In the case of an isometric contraction, no work is done since there is no travel. At the other end of the spectrum, lower forces are needed for contractions of 12 to 18 cm length. FIG. 2 illustrates the force required to deliver an energy per contraction of 0.75 joules, 1.25 joules, 1.75 joules, and 2.65 joules for stroke lengths up to 15 cm. The approximate work required for an intraaortic balloon pump or other types of aortic counterpulsation devices in a skeletal muscle system is on the order of 0.75 joules per contraction with passive deflation (where systolic arterial pressure provides the force for deflation), or 1.25 joules using spring augmented deflation; a ventricular assist device requires about 1.75 joules per contraction; and a total artificial heart requires 2.25 joules. Referring to FIG. 3, in which the data of FIG. 2 has been enlarged, it is shown that a force of 4 to 5 kg, with a stroke energy of 0.75 to 2.65 joules, requires a stroke length of 2 to 5 cm. Therefore, a single skeletal muscle would be required to contract with approximately 3 to 8 kg of force per stroke and have a stroke length of approximately 2 to 4 cm in order to power the desired range of devices. Alternatively, two muscles, each generating less energy per contraction, could be arranged such that their combined contractile energy would provide sufficient power for the particular device desired.

The skeletal muscle must be able to sustain this level of work, not just for one contraction, but over long periods. If, for example, the work per stroke was 1.75 joules and the pumping rate was 60 beats per minute (one per second), the power output of the muscle would need to be 1.75 watts. The power available from skeletal muscle has been estimated to be 3 to 15 mW per gm (Geddes, et al., (1991), *Trans. ASAIO*, 37:19-23), so a muscle mass of about 116 to 350 grams is generally sufficient to power the range of circulatory support systems within the scope of the present invention.

Since circulatory support devices are intended to be used in older patients with heart failure, there undoubtably would be some drop in skeletal muscle output, perhaps even as much as 75% by the age of 65 (Borne, The Structure and Function of Muscle, 2nd Ed., Academic Press, 1973). However, since some of this loss may be due to inactivity of the muscle, it is predicted that a portion may be partially reversible with training and further dimunition of the muscle output could be retarded. A force of 3 to 8 kg is thus a reasonable assumption of available force obtainable from a major skeletal muscle.

The latissimus dorsi, pectoralis, psoas major, and rectus abdominis muscles are examples of the major skeletal muscles capable of supplying sufficient power output, after training, to drive a full range of circulatory support devices. This is especially true when the muscle is left in-situ and, with a normal pre-stretch, and pulls in tension rather than squeezes, as is the case when the muscle is wrapped around the heart or a pump bladder.

Contractions of major skeletal muscles, such as the latissimus dorsi, range from a maximum of 57% of original length ("$l_o$") of the muscle to no contraction (isometric contraction). Although near maximum force can be developed in skeletal muscle under isometric contraction conditions, no work is done unless the muscle actually contracts and moves through some distance. Contractions in the range of 20 to 30% of $l_o$ are considered quite normal.

The original length, $l_o$, for the latissimus dorsi muscle in small women is around 30 cm, while for a large man, it would be about double this length, or around 60 cm. Contractions of 20% to 30% would mean movement of the tendon at the distal end of the latissimus dorsi of 6 cm for a small woman to as much as 18 cm for a large man with a longer contraction length. Thus, the latissimus dorsi is capable of supplying the preferred stroke length in the skeletal muscle energy conversion system of the preferred embodiment.

In addition to stroke length, the time required for contraction is also important. For beat rates of 70 to 80 beats per minute, the systolic and diastolic intervals are 300 to 500 msec. A stroke length of 4 cm with a contraction time of 300 msec would require an average velocity of 13.3 cm/sec. However, 13.3 cm/s is a fast contraction for any skeletal muscle, and is particularly fast for a large muscle such as the latissimus dorsi. Obviously, a shorter stroke length results in lower contraction velocities. Thus, the optimum design of the present invention would include a shorter stroke length favoring lower contraction velocities and a higher exerted force.

Overview of a Muscle Energy Conversion System

The function of the energy conversion system is to convert mechanical work available from the muscle in the form of a force acting over a distance, into energy necessary to actuate a blood pump for partial or complete circulatory assistance, or to actuate any implanted medical device. The energy conversion system includes an implantable energy convertor/actuator connected to a skeletal muscle for converting energy extended in the linear contraction of a muscle into a transmutable energy form. In a preferred embodiment, the force is converted by the energy convertor/actuator into a hydraulic pulse needed to drive a blood pump in the form of a volume change of a fluid delivered at a pressure differential. However, pneumatic or electromagnetic force may also be produced. Where the energy is in hydraulic or pneumatic form, the energy convertor/actuator is preferably a cylinder anchored to the skeleton, with a piston attached to the muscle. Where the energy is electrical, the energy convertor/actuator anchored to the skeleton preferably contains a coil surrounding a magnet which is attached to the muscle, thus contraction of the muscle moves the magnet past the coil, inducing an electric current to flow in the coil.

Figure 5:
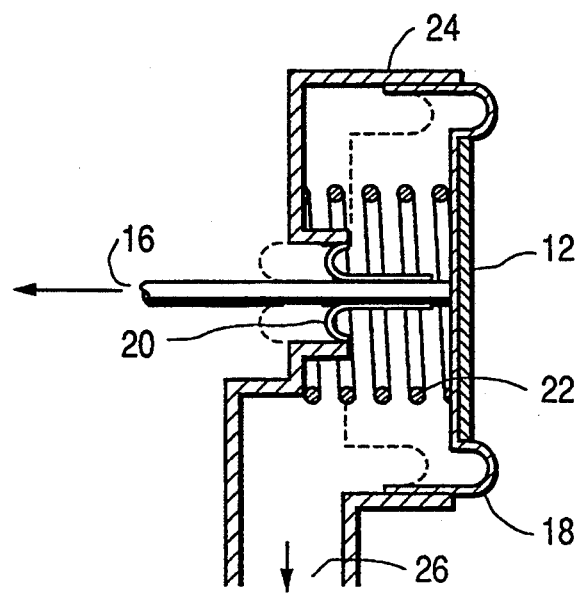
FIG. 5 is a schematic illustration of the operation of the system shown in FIG. 4.
Figure 4:
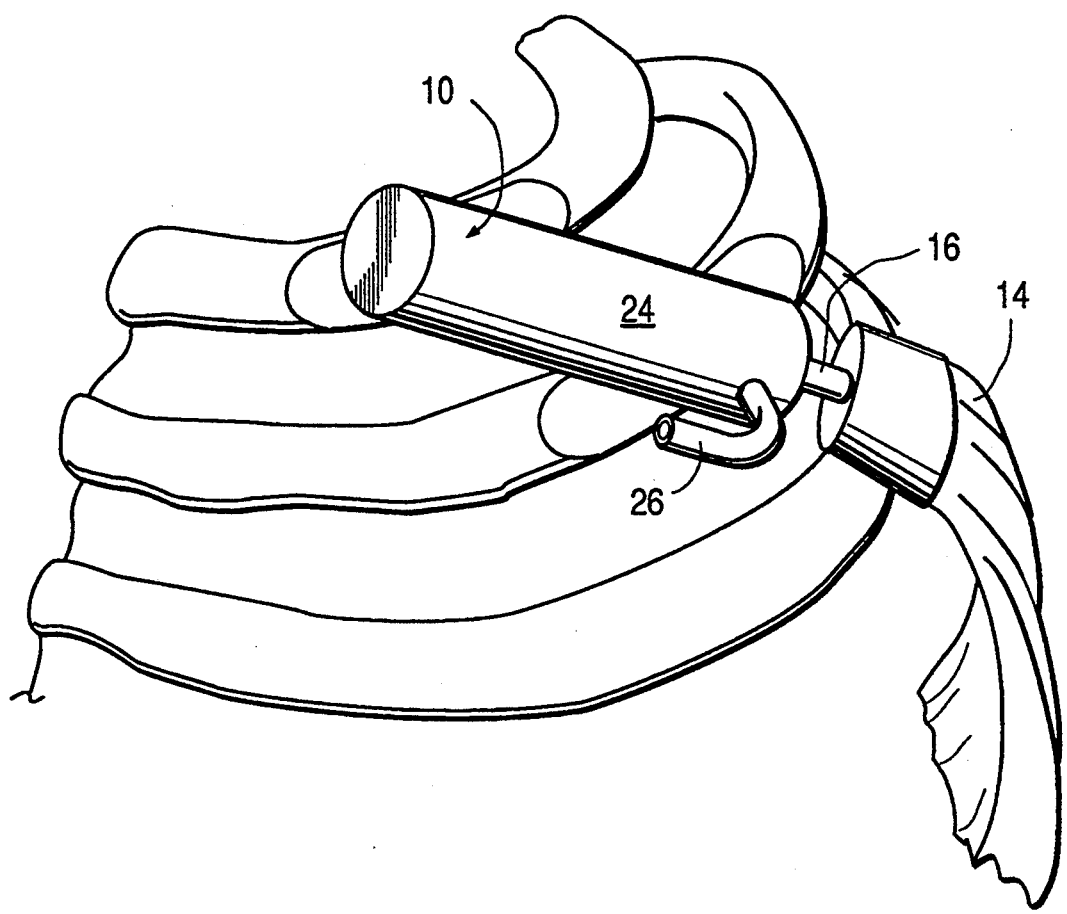
FIG. 4 illustrates the skeletal muscle energy conversion device according to one embodiment of the invention.
Figure 6:
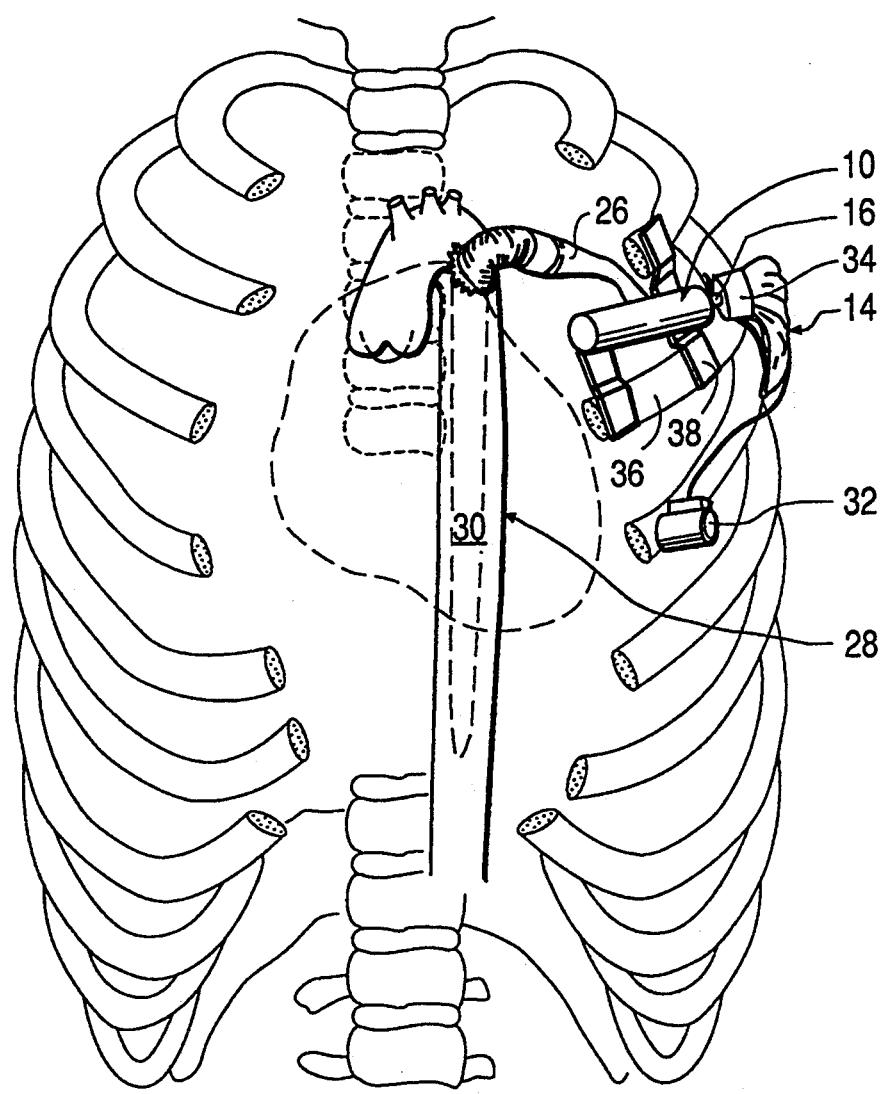
FIG. 6 illustrates the energy conversion system as implanted.

Referring to FIGS. 4 and 5, the simplest form of a convertor/actuator 10 is a hydraulic piston 12, where pressure is developed and fluid is displaced as the muscle 14 contracts and applies tension to the shaft. In the illustration shown in FIG. 5, both the piston and shaft seals 18 and 20, respectively, are rolling diaphragms, however, bellows or other types may of course be utilized. The spring 22 may optionally be used to return the piston 12 in order to perform the next cycle. The linear contractile force of the muscle 14, which is connected to the convertor/actuator piston shaft 16, causes movement of the piston 12 resulting in displacement of the hydraulic fluid within the cylinder 24. This low pressure fluid is then transmitted via a hydraulic transmission line 26 to an implanted medical device. As shown in FIG. 6, the transmission line 26 delivers the energy from the convertor/actuator 10 to an implanted medical device 28 such as the intraaortic balloon 30 which is illustrated.

FIG. 6 also illustrates the attachment of the skeletal muscle conversion system, where muscle 14 is attached to the piston shaft by muscle attachment means and the cylinder 24 is firmly anchored by plates 38 to the skeleton 36 such that the muscle linearly contracts against a rigidly fixed convertor/actuator 10 for most efficient transfer of energy. Contraction of the muscle 14 is stimulated in a controlled fashion by stimulator means 32.

Figure 7:
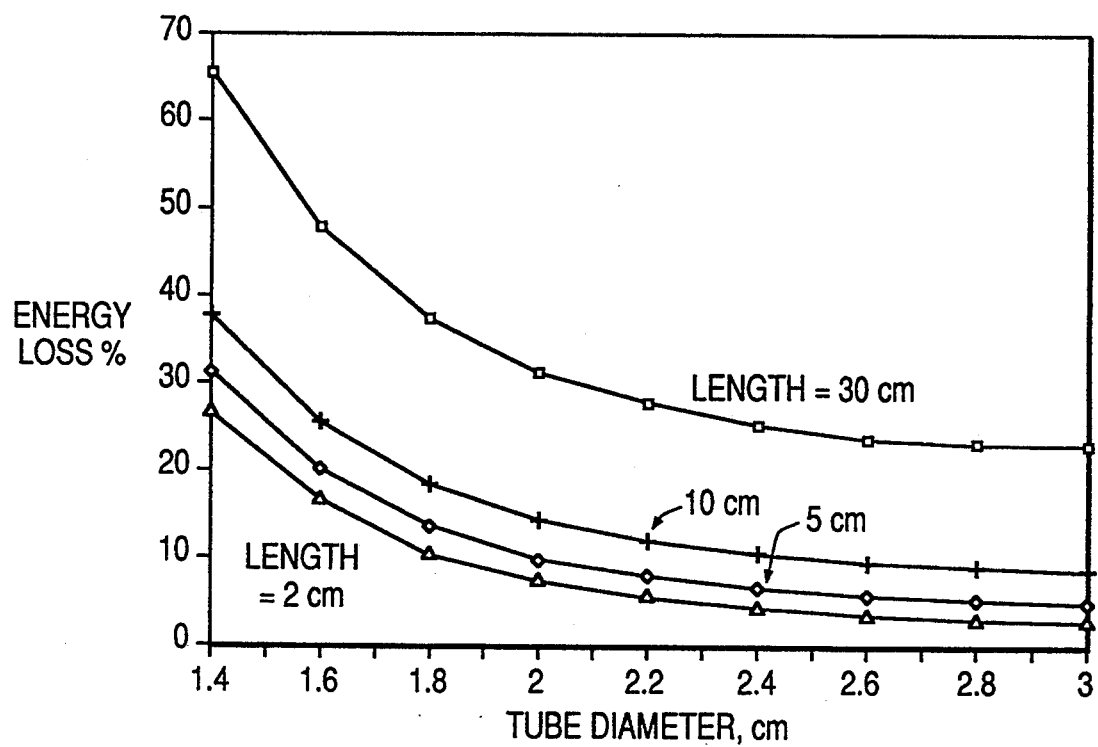
FIG. 7 is a graphical representation of the energy losses in hydraulic transmission between the skeletal muscle energy convertor/actuator and an implanted medical device requiring 0.75 joules per stroke for operation.

In its simplest form the pressure of the convertor/actuator 10 is at physiologic pressure. Physiological pressures are generally defined herein as the pressure in the circulatory system. For example, the right ventricle pumps into the pulmonary arteries against pressures of from about 0.5 to about 1.0 psi, while the left ventricle pumps into the aorta against pressures of from about 2.0 to about 4.0 psi, more usually from about 2.5 to about 2.8 psi. Where the system operates at physiological pressure, displacement of the hydraulic fluid must equal the stroke volume of the intraaortic balloon 30 or other similar types of blood pumps. Alternately stated, since the muscle 14 is connected directly to the piston shaft 16, muscle travel must equal piston travel, and since the piston output is connected directly to the blood pump 28, a one-to-one relationship is thereby created. This type of system is a simple mechanism to convert energy, but as depicted in FIG. 7 for a typical counterpulsation blood pump, it has the disadvantage that losses in the hydraulic fluid operating at physiological conditions are large and increase significantly with the length of the transmission line between the implanted medical device. In addition, the transmission line tube diameter must be large or the losses are also unacceptably large. These considerations lead to the desirability of locating the components that generate hydraulic energy at physiological fluid flow levels as close as possible to the blood pump, or other implanted device, but without moving the muscle.

Alternatively, a high pressure-low volume convertor/actuator can be utilized with high pressure hydraulic fluid. Since hydraulic losses are minimum at low flow rates obtained by utilizing high pressure, more versatility is thereby obtained for locating the convertor/actuator. The high pressure hydraulic energy can then directly actuate an implanted medical device such as a pusher plate blood pump, similar to the pneumatic pusher plate pump shown in FIGS. 8 and 9.

Figure 8:
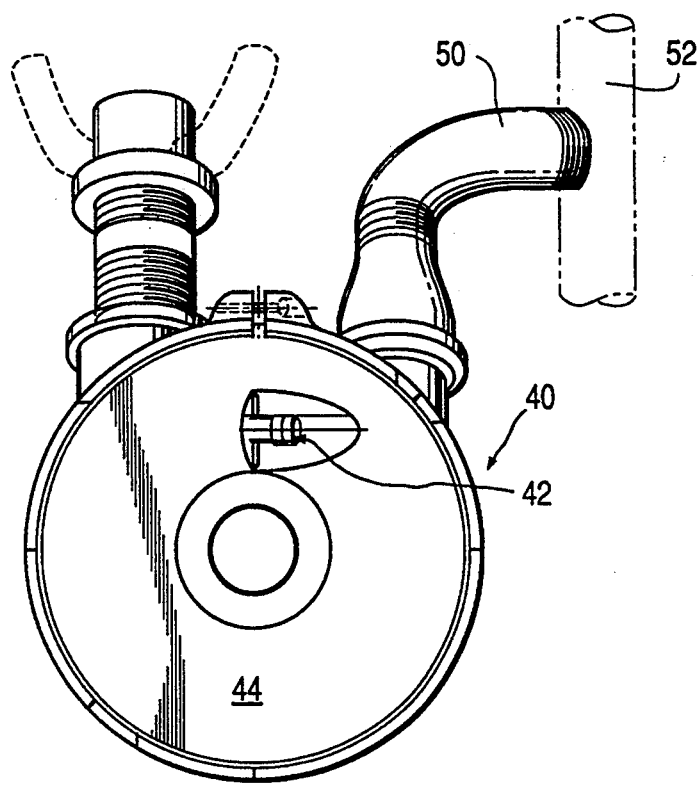
FIG. 8 is an illustration of a pneumatically actuated pusher plate blood pump of the prior art.
Figure 9:
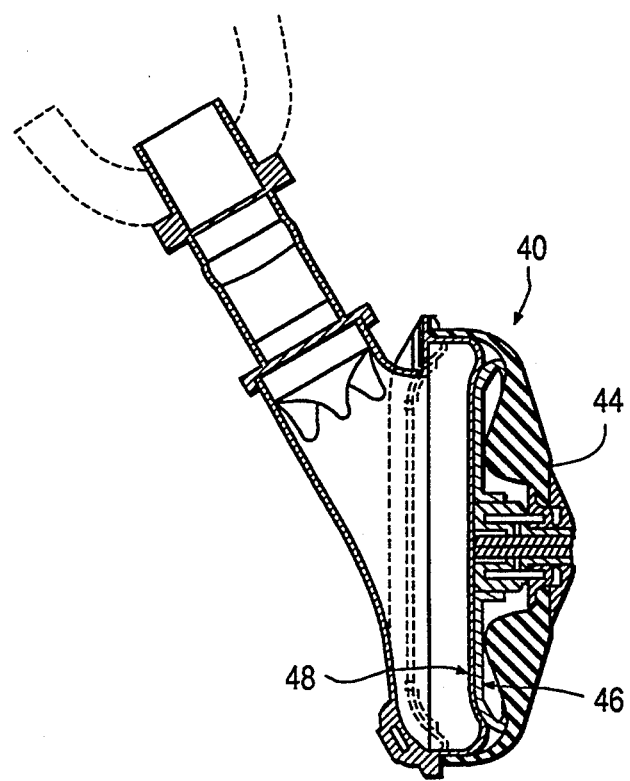
FIG. 9 is a cross-sectional view of the blood pump shown in FIG. 8.

In prior art pump 40 shown in FIGS. 8 and 9, pneumatic energy is introduced through pneumatic port 42 into pump housing 44 behind pusher plate 45, forcing pusher plate 46 to compress blood-containing bladder 48. Upon compression, blood is expelled from bladder 48 into outflow cannula 50 and thence into the aorta 52.

Figure 10:
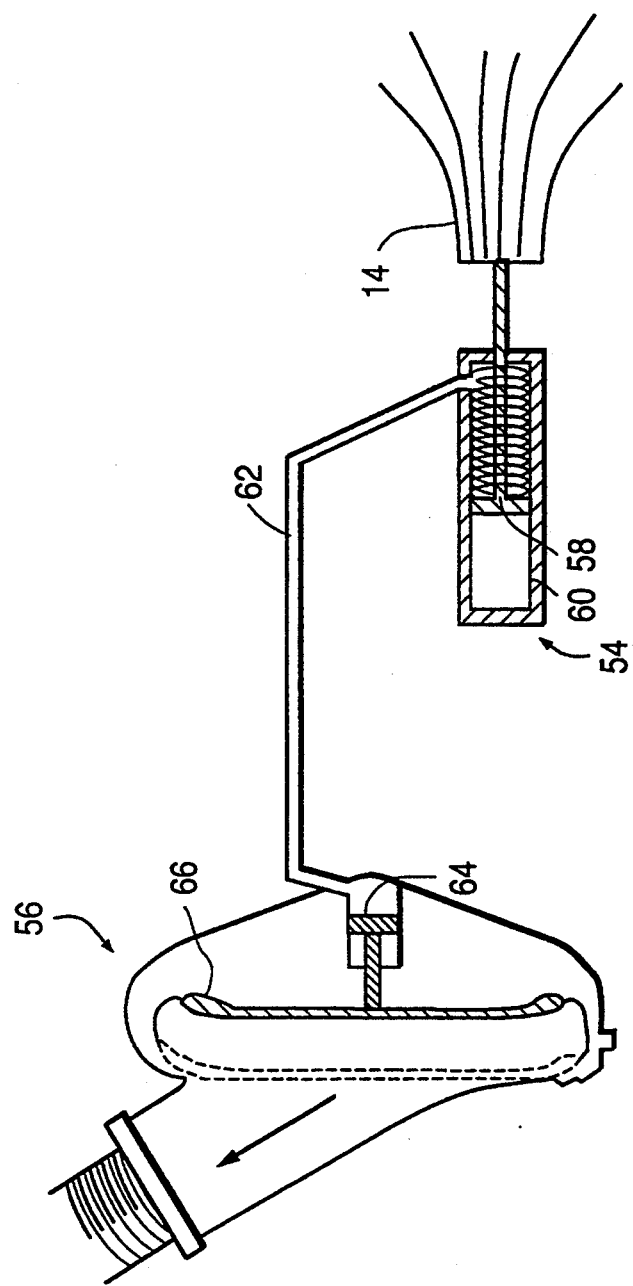
FIG. 10 illustrates the skeletal muscle energy conversion system according to another embodiment.
Figure 11A:
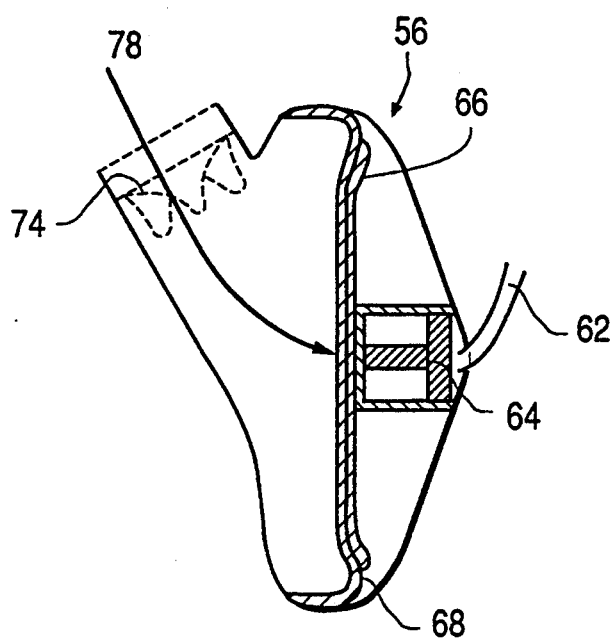
FIG. 11 is a schematic illustration showing the operation of the blood pump shown in FIG. 10.
Figure 11B:
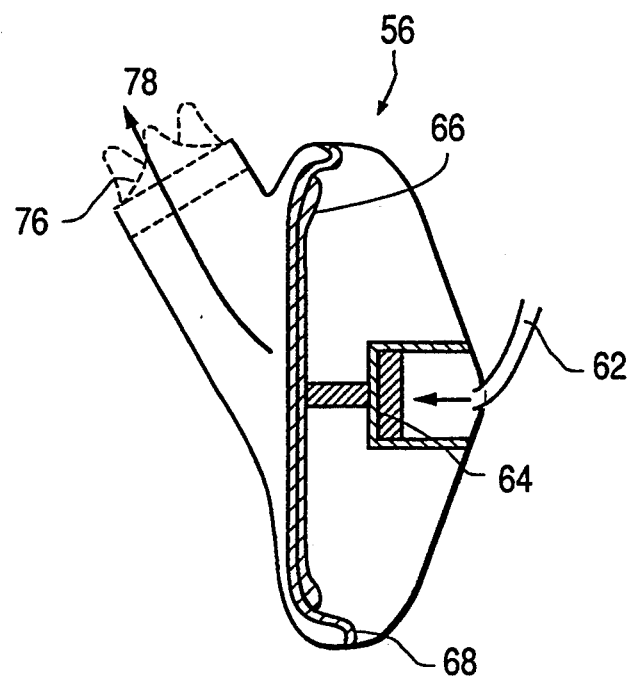
Figure 12:
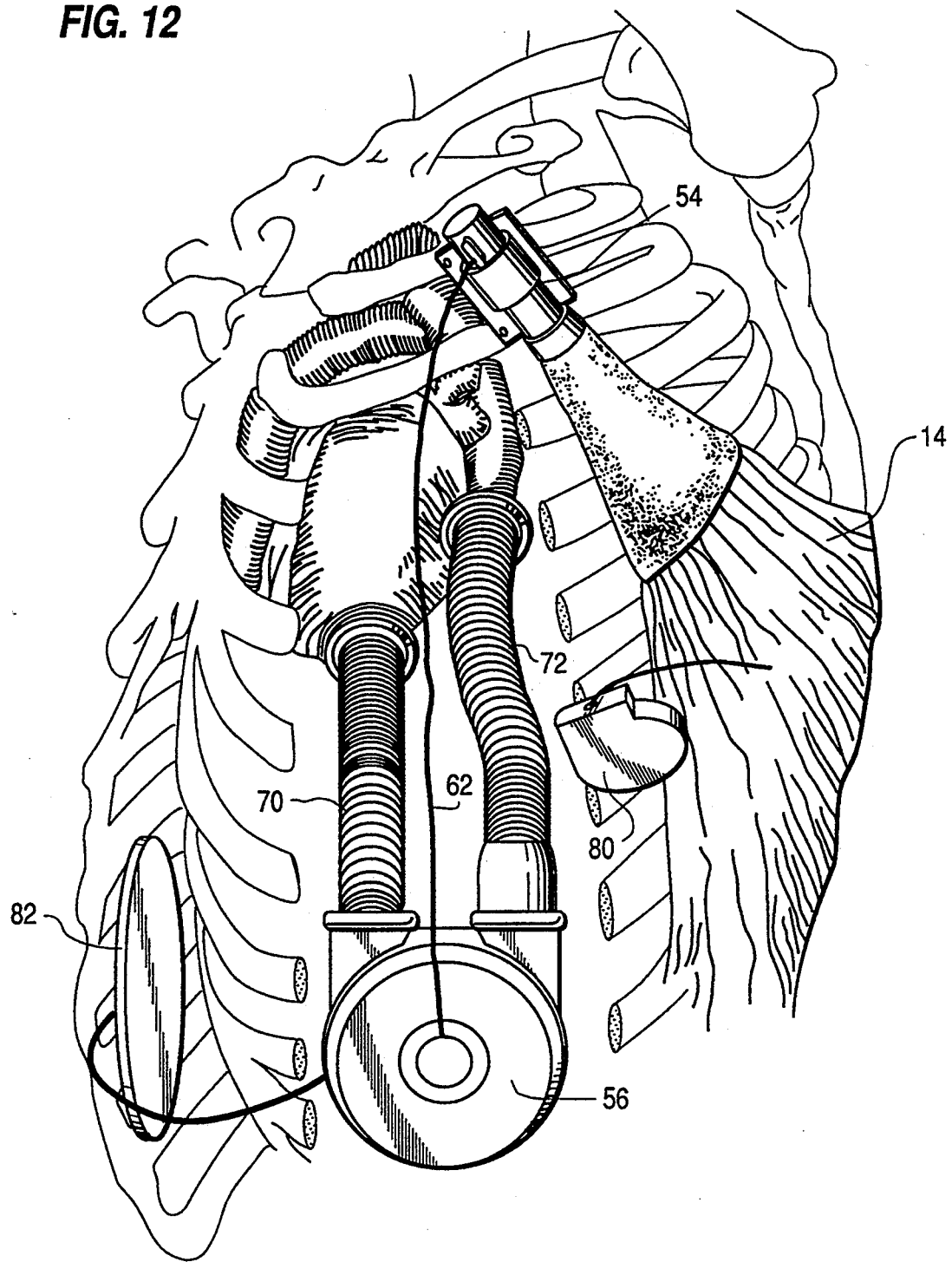
FIG. 12 illustrates the energy conversion system of FIG. 10 as implanted.

Referring to FIGS. 10-12, a high pressure convertor/actuator 54 is connected between the muscle 14 and a modified pusher plate blood pump 56. In this embodiment, contraction of the muscle 14 moves the piston 58 within the cylinder 60 of the convertor/actuator 54 causing high pressure hydraulic fluid to be displaced. The hydraulic fluid, via a transmission line 62, then moves the small diameter piston 64 of the blood pump 56 causing the pusher plate 66 to compress bladder 68 and expel blood from the pump at a lower pressure but higher displaced volume.

FIG. 11A shows the inflow of blood 78 from inflow cannula 70 via a one-way valve 74 to fill bladder 68. Transmission of a small volume of hydraulic fluid via high pressure transmission line 62 moves small diameter piston 64, causing pusher plate 66 to compress bladder 68 expelling a large volume of blood into outflow cannula 72 through a one-way valve 76 at physiological pressure. In this instance, the energy within the high pressure low volume hydraulic fluid causes movement of a high volume of blood at low physiological pressure. A spring may also be used to aid in the blood pump filling and muscle lengthening shown in FIG. 11A, and either bellows or rolling diaphragm seals can be used as in the first embodiment described herein.

As shown in FIG. 12, it would be obvious to the skilled in the art to include a variable volume compensator similar to that required with the total implantable electromechanical ventricular assist systems or artificial hearts. The compensator is based on state of the art technology developed in the NHLBI programs. FIG. 12 also shows stimulator means 80 used to stimulate controlled contraction of the muscle 14.

Figure 13:
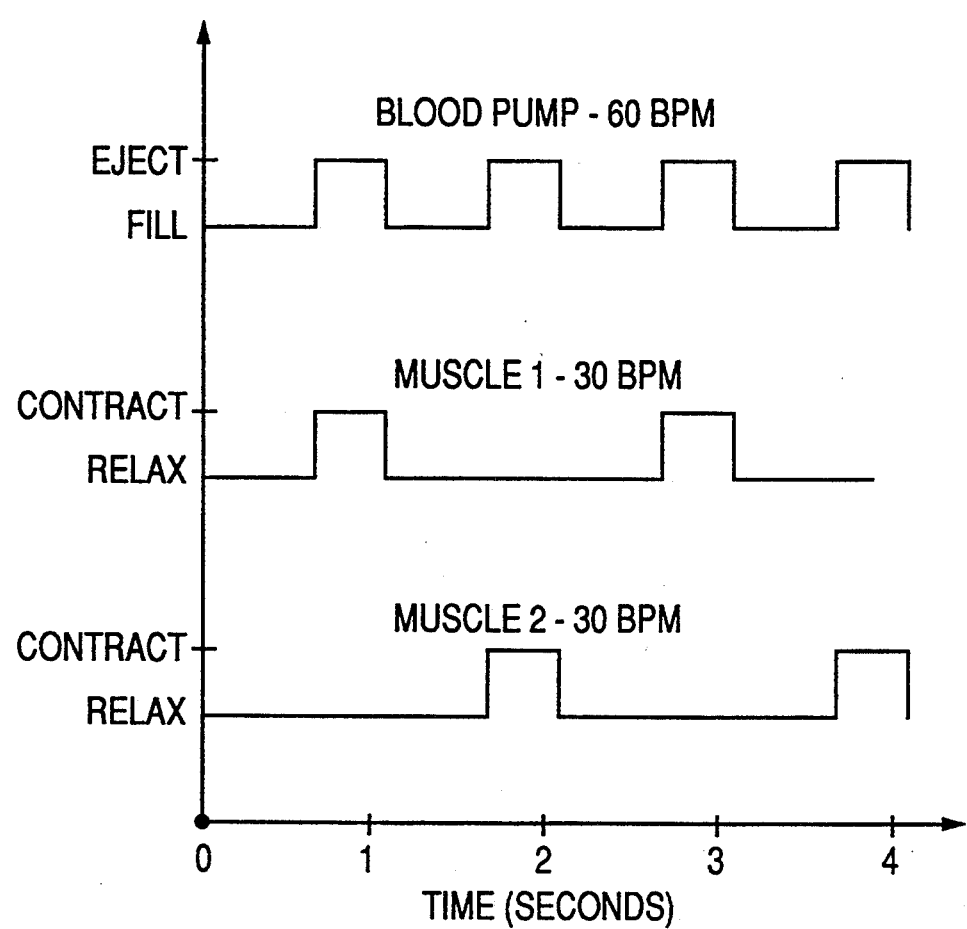
FIG. 13 graphically represents a timing cycle for a two-muscle energy conversion system.
Figure 14A:
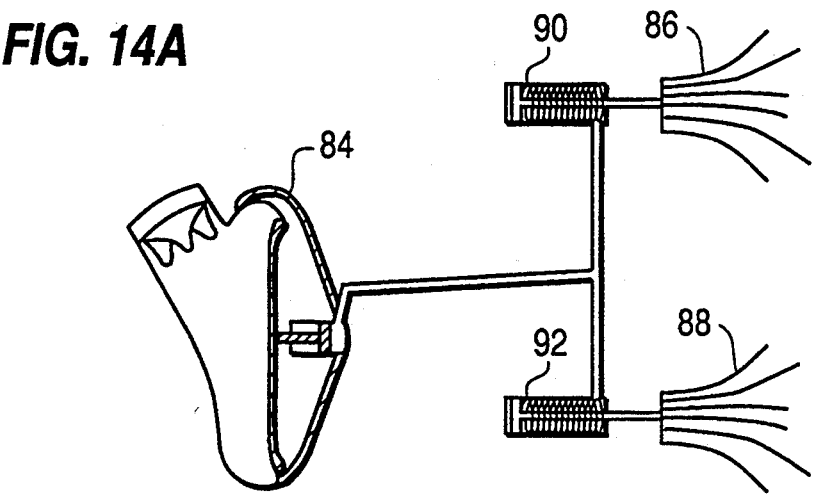
FIG. 14 is a simplified schematic illustration showing the operation of a blood pump coupled to a two-muscle energy conversion system.
Figure 14B:
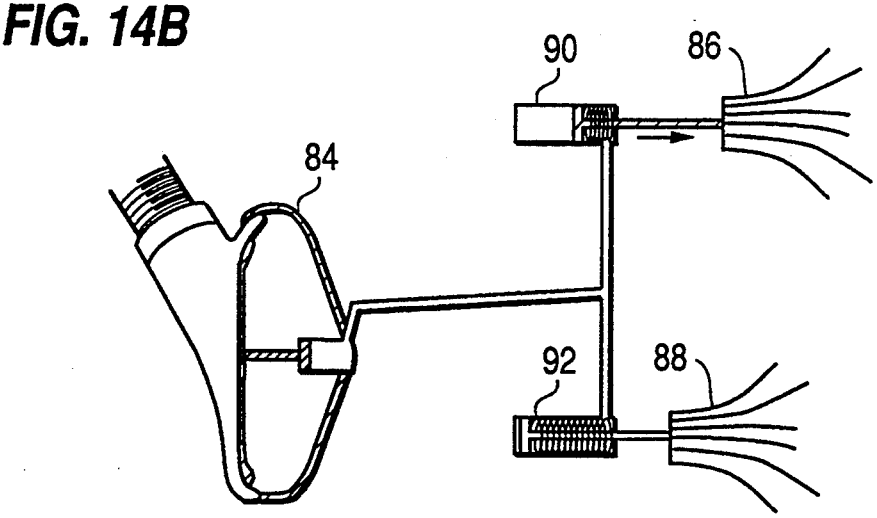
Figure 14C:
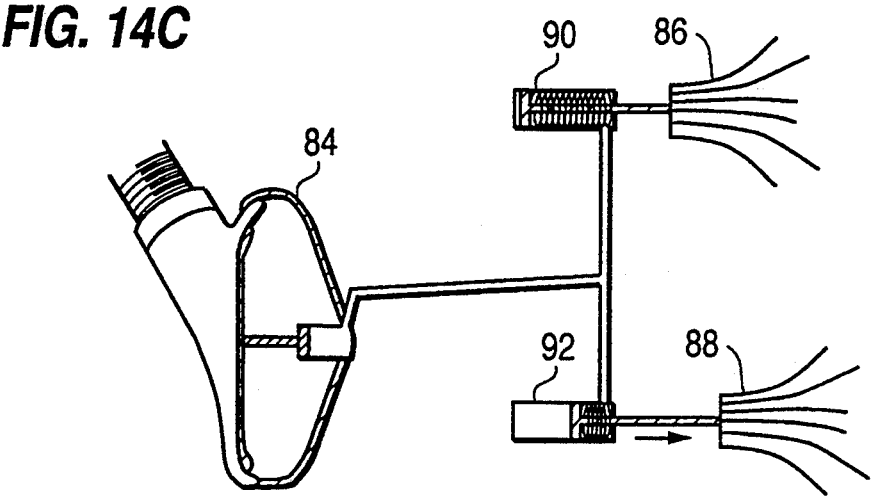
Figure 15:
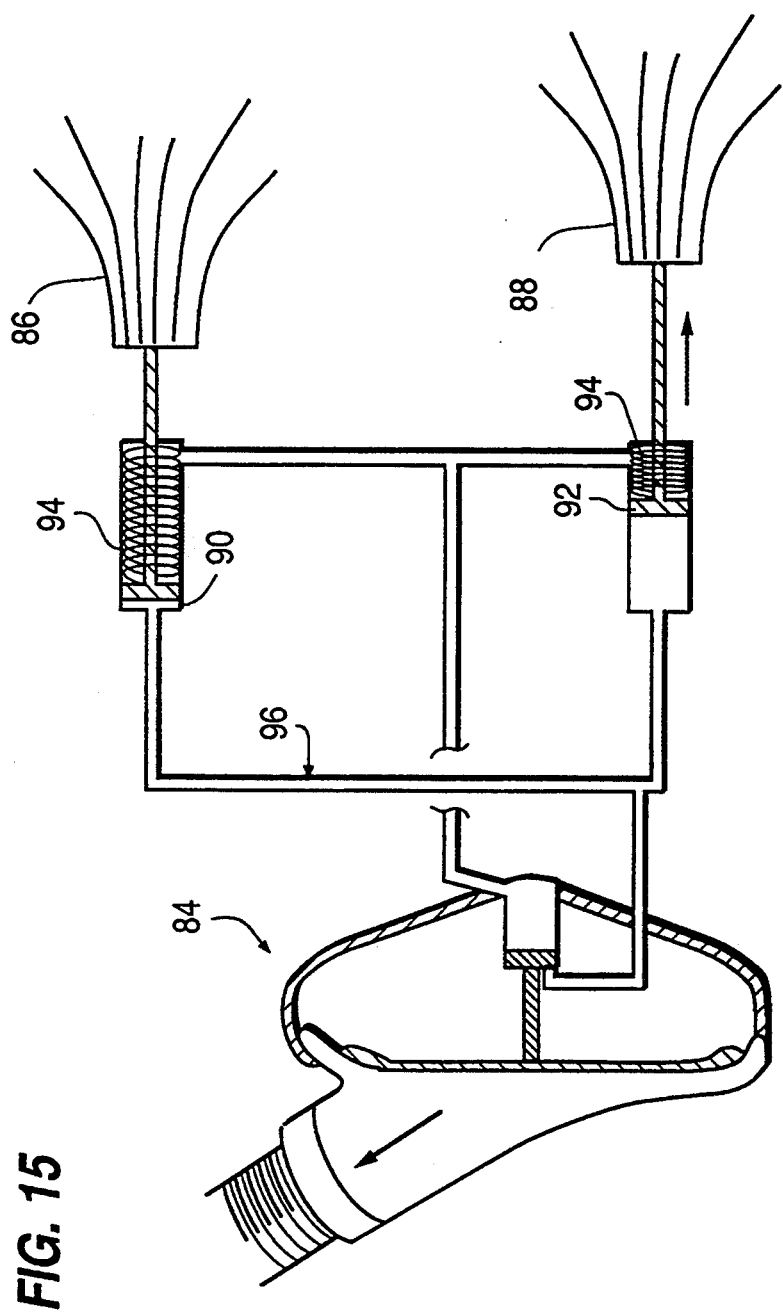
FIG. 15 is a simplified schematic illustration of a preferred embodiment of the system shown in FIG. 14.

Referring to FIGS. 13-15, a two muscle alternate contraction system and the preferred timing therefor is illustrated. Where the skeletal muscle energy conversion system is driving a pulsatile blood pump, and the desired pulse rate of the blood pump exceeds the repeat rate of contraction usually expected of conditioned skeletal muscle, this system allows two muscles to be used to produce a combined pulse rate of high pressure hydraulic energy that is greater than the repeat contraction rate of either muscle. FIG. 13 illustrates an example of a pump rate of 60 beats per minute (bpm) and a muscle contraction rate of 30 bpm. As shown in FIG. 14A, when the blood pump is filling both muscles 86 and 88 are relaxed. When muscle 86 contracts, the blood pump 86 ejects as shown in FIG. 14B. When muscle 88 relaxes, therefore, its piston 92 is fully extended and no hydraulic valve is necessary, although one could be added. In FIG. 14C, muscle 88 contracts, also resulting in blood pump ejection. FIG. 15 shows a preferred embodiment including an optional spring 94 which augments muscle lengthening and return of pistons 90 and 92 and also a vent line 96.

Although the high pressure embodiment described herein is illustrated in conjunction with a pusher-plate blood pump, it will be apparent to one skilled in the art that any such implanted medical can device can be operated by the high pressure hydraulic energy produced by this embodiment. In particular, circulatory support devices such as high pressure centrifugal pumps may be utilized, for instance in an atrial-aortic shunt similar to the one described in U.S. Pat. No. 4,995,857.

The use of high pressure transmission lines minimizes the hydraulic losses experienced at physiological pressure. However, many implanted medical devices, and in particular circulatory support devices, require low pressure fluid for operation. Thus, an intermediate device operating at higher pressure but lower displaced volume is preferred to efficiently transmit the energy from the muscle to the implanted device.

Figure 16:
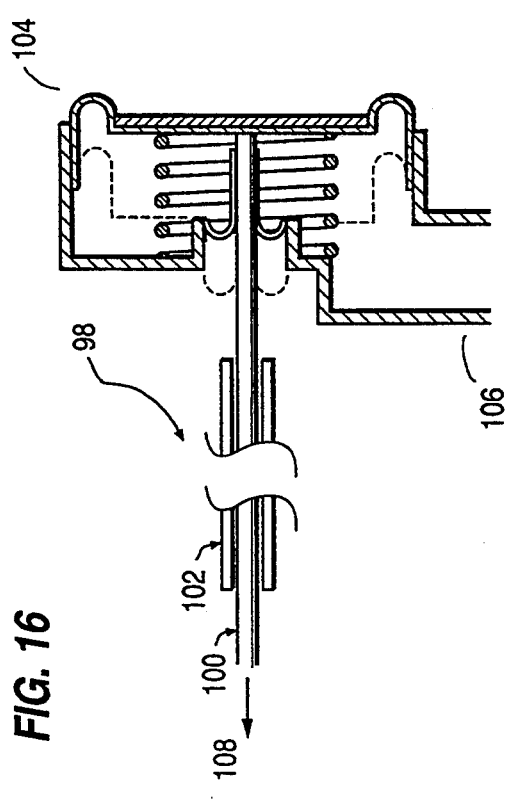
FIG. 16 is a schematic illustration of a mechanical device for transmitting energy to an implanted medical device.
Figure 17:
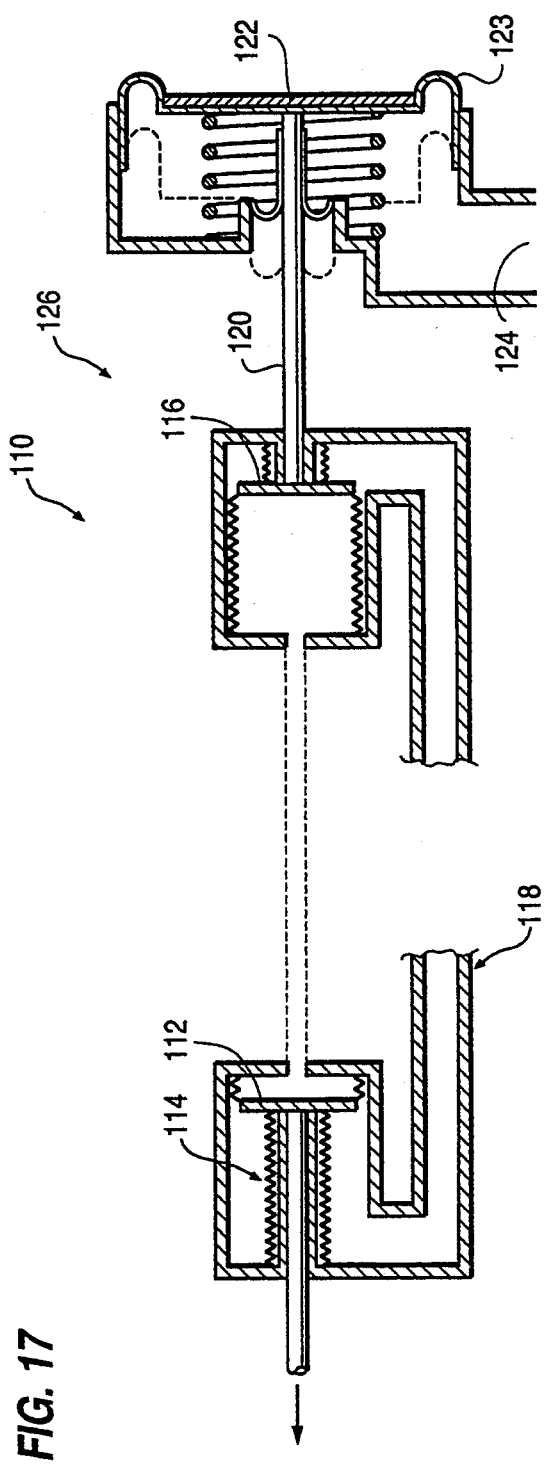
FIG. 17 is a schematic illustration of a hydraulic device for conversion of hydraulic energy transmitted at high pressure to low pressure hydraulic energy for operation of an implanted medical device.

In the present invention, two alternate techniques are described for accomplishing this task—mechanical and hydraulic transmissions, as shown schematically in FIGS. 16 and 17. The mechanical transmission 98 includes a rod or cable 100 running in a tunnel 102 connecting the muscle attachment to the actuator 104 which drives an implanted medical device. Input muscle contraction force is transformed, in this instance, to low pressure hydraulic power, within the hydraulic fluid exiting hydraulic transmission line 106, which thereby operates the implanted medical device, such as a blood pump. The tunnel would need to be sealed to prevent entrance of body fluids and would require careful design to minimize friction and wear. The hydraulic transmission 110 includes a piston 112 with a shaft 114 directly connected to the muscle attachment so that muscle contraction causes the development of pressure and flow of a fluid in a closed container. A hydraulic actuator 126 located close to the implanted medical device converts this transmission pressure, with a small fluid displacement, to a larger displacement of fluid at a physiological pressure. That is, high pressure hydraulic fluid enters small piston 116 via hydraulic transmission line 118 and the power therein is transferred via mechanical connection means 120 to a larger volume piston 122 which then displaces low pressure hydraulic fluid through low pressure transmission line 124 to operate an implanted medical device. Each fluid compartment must be contained in a closed volume. By proper selection of transmission pressure and tube size, transmission losses can be reduced to a negligible level.

The characteristics of a hydraulic actuator in terms of operating conditions, tubing size and energy losses are analyzed below. The generation and delivery of a quantity of hydraulic fluid equal to the stroke volume at physiological pressures is common to all conversion concepts in this analysis; therefore, similar losses occur in all cases. Losses considered in this analysis include viscous losses in the tube connecting the actuator to the blood pump, inertia losses in this tube reflecting the energy required to accelerate the fluid in the tube at the start of each stroke, kinetic energy losses that result from the imperfect conversion of kinetic energy in the fluid back into potential energy as it reaches the blood pump, and compliance losses that result from the elasticity of the connecting tube and other components.

Figure 18:
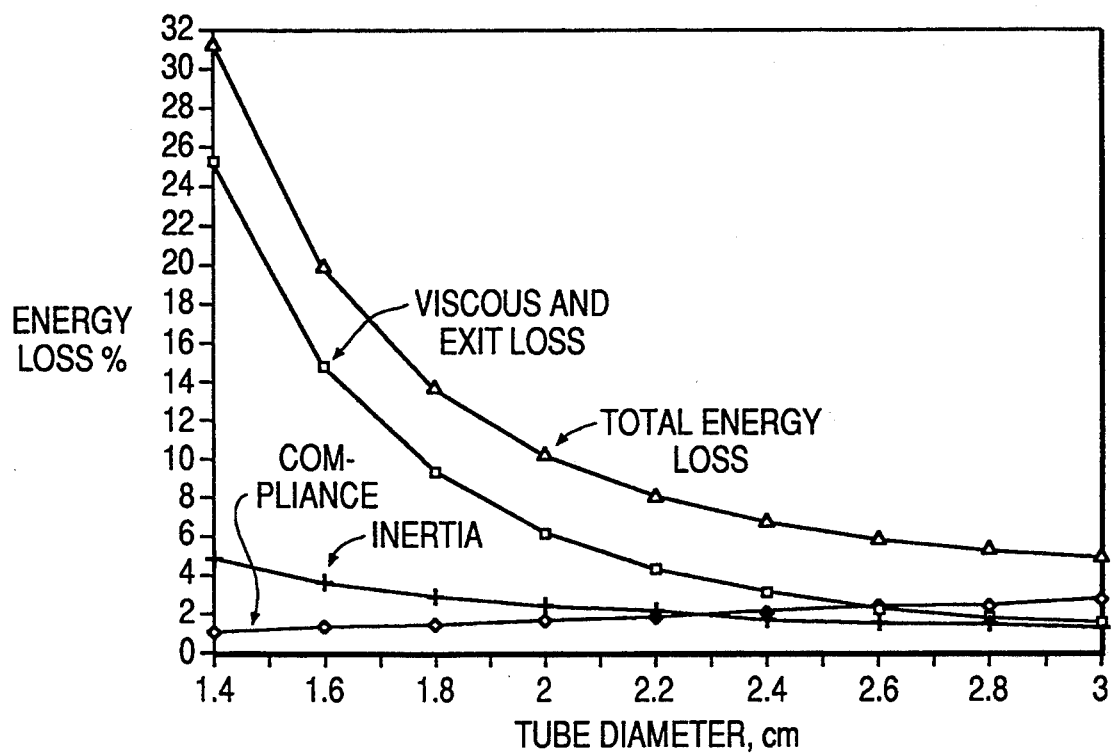
FIG. 18 is a graphical representation of the energy losses in hydraulic transmission through a 5 cm tube between a skeletal muscle energy convertor/actuator and an implanted medical device.

Referring back, FIG. 7 shows the losses that result from the use of an actuator operating at physiological pressure and stroke volume as a function of connecting tube diameter and length. A distance between the actuator and the blood pump(s) of 10 to 30 cm would result in relatively large losses. However, a length of only 2 to 5 cm would be necessary if the actuator was located adjacent to the blood pump. In this case, the losses would be much smaller. Losses are also reduced with a larger tube diameter or with specially-shaped tubes (oval rather than round, for instance). However, a diameter of more than 1.8 to 2.0 cm may not be possible due to blood pump size limitations. FIG. 18 shows the distribution of losses among the various fluid loss elements for a tube length of 5 cm in a counterpulsation device requiring 0.75 joules/strike for operation.

Figure 19:
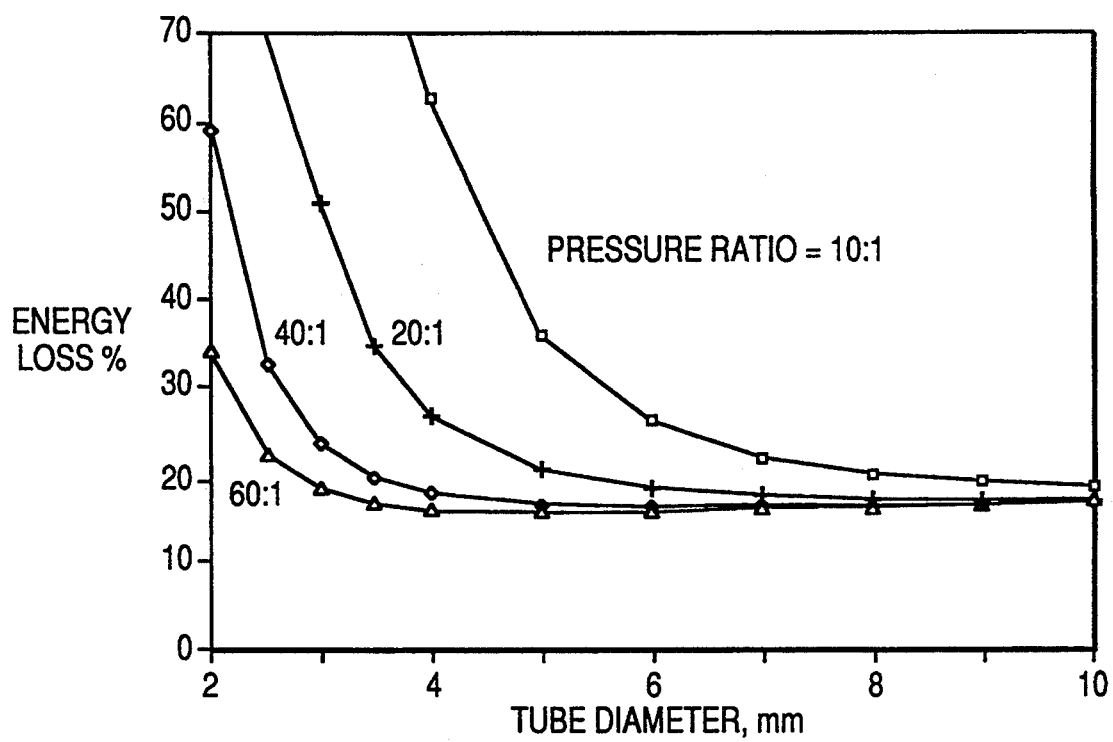
FIG. 19 is a graphical representation of the energy losses in hydraulic transmission through a 30 cm length of tube between a skeletal muscle energy convertor and the actuator of an implanted medical device requiring 0.75 joules per stroke at various transmission pressures.
Figure 20:
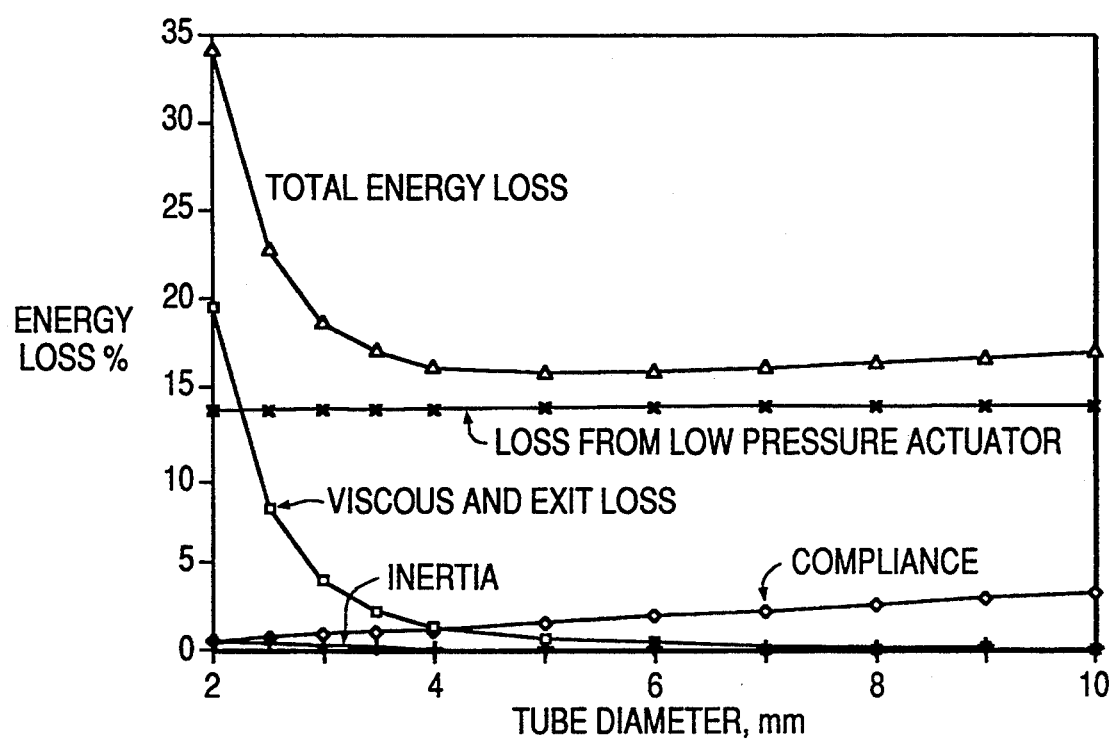
FIG. 20 is a graphical representation of the energy losses in hydraulic transmission between a skeletal muscle energy conversion system and an implanted medical device requiring 0.75 joules per stroke using two-stage hydraulic activation.

The results of similar calculations performed for the preferred embodiment utilizing an intermediate transmission pressure are shown in FIGS. 19 and 20. Since a high pressure to low pressure actuator is used in this embodiment, a tube diameter of 1.8 cm and a length or 5 cm is assumed, and losses for this actuator are added to the losses attributable to the transmission pressure conversion. Losses from the transmission are similar to those described above except they are much lower and tube diameters are smaller (FIG. 19). The contribution of various loss elements for a transmission pressure to physiological pressure ratio of 60:1 is shown in FIG. 20.

The preferred embodiment of the hydraulic transmission is achieved by utilizing a high pressure energy convertor and a two-stage hydraulic actuator which allows considerable flexibility in locating components. By locating the high pressure energy convertor in close proximity with the latissimus dorsi (or other suitable muscle), it allows the muscle to be left basically in-situ with minimal manipulation, yet maximum mechanical advantage anti efficiency are obtained by the linear alignment of the energy convertor. A small diameter hydraulic line connects the convertor with the actuator, which for maximum fluid dynamic efficiency is located as close to the heart as possible. Because of the low losses in the transmission line the actuator and blood pump can be placed intrathoracically or intraabdominally, or elsewhere as required.

Figure 21:
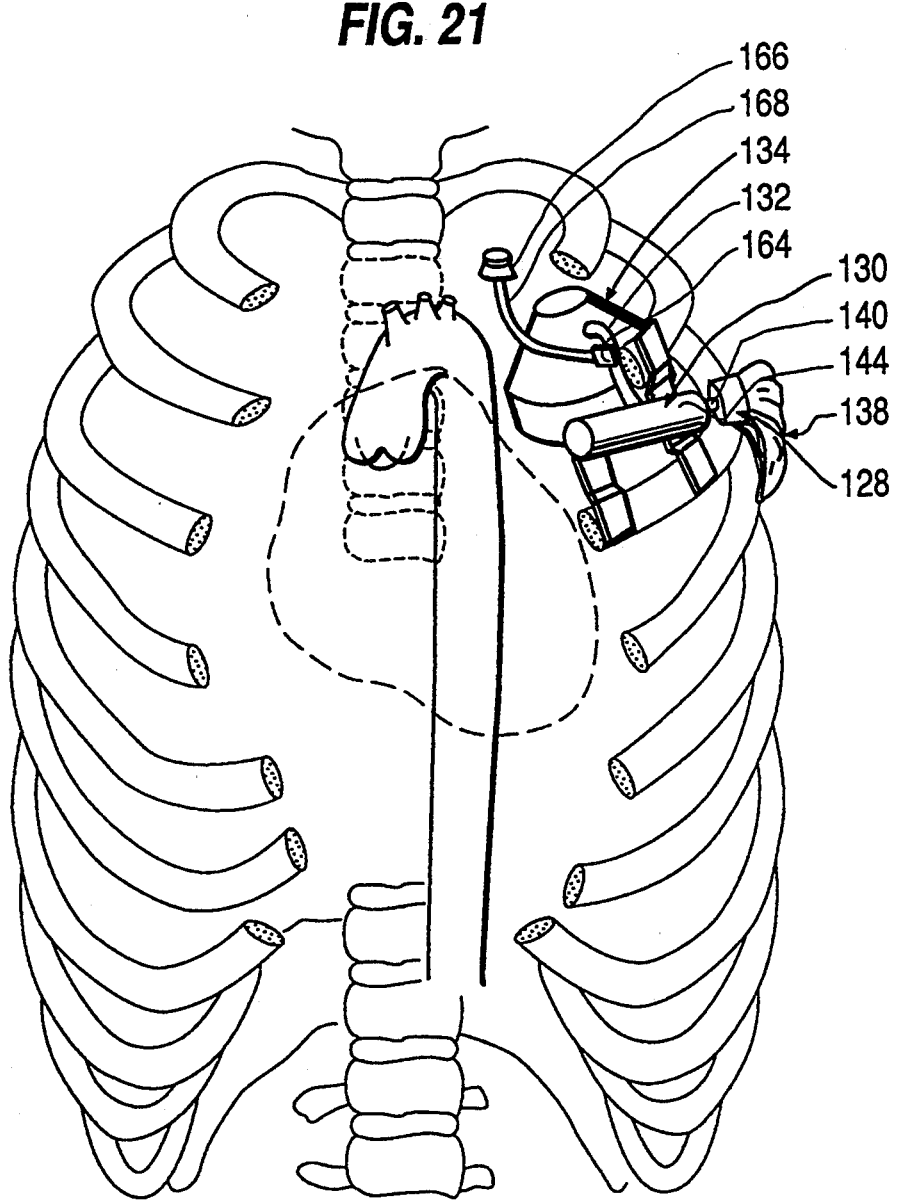
FIG. 21 illustrates a preferred embodiment of the skeletal muscle energy conversion system as implanted.

As shown in FIG. 21, a preferred embodiment of the energy conversion system includes muscle attachment means 128, a hydraulic convertor 130, interconnecting tubing 132, a two-stage hydraulic actuator 134, and an implanted medical device.

Figure 22:
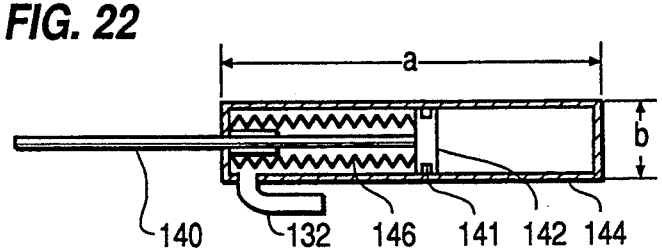
FIG. 22 is a schematic representation of the hydraulic convertor of FIG. 21.

Referring also to FIG. 22, the insertion end of the latissimus dorsi muscle 138, or other suitable muscle, is connected to the piston shaft 140 of the hydraulic convertor 130. The hydraulic convertor 130, shown schematically in FIG. 22, includes a stainless steel, titanium, or other physiologically compatible cylinder 144 having a length "a" of approximately 6.35 cm and a diameter "b" of approximately 1.15 cm. The piston 142, designed to generate hydraulic pressure and flow when pulled in tension by the latissimus dorsi muscle 138, is contained in the center of the cylinder 144. The piston 142 and piston shaft 140 are also made of stainless steel, titanium, or other physiologically compatible material and is designed to have a close fit within the cylinder in order to minimize hydraulic losses. There is a welded titanium bellows 146 that seals this hydraulic fluid space from the body's extracellular fluid space, as discussed in detail below. The convertor 130 has screw fittings which permit its rigid attachment to the rib cage, as also described below. The convertor 130 can be linear for simplicity or curvilinear for better anatomical fit at the rib cage. A high pressure hydraulic transmission line 132 carrying hydraulic fluid preferably at a transmission pressure of approximately 80–200 psi, with a fluid displacement of approximately 1.4 ml, connects the convertor 130 to the hydraulic actuator 134 located inside the thoracic cavity at its left apex above the lobe of the superior left lung. This line 132 preferably has an outside diameter of generally 0.45 cm with a wall thickness on the order of 0.05 cm. All connections are welded, forming leak-tight hermetic seals.

The convertor 130 is enclosed in a relatively soft polyurethane encapsulation in order to minimize damage to any tissues coming into repeated contact with the actuator. The outer surfaces of the polyurethane are designed to form a controlled amount of tissue ingrowth in order to avoid an open pocket or sinus tract in which infections can develop. The piston 142, including the piston shaft 142 attaching to the latissimus dorsi muscle, or other muscle, is enclosed in a smooth polyurethane cone-shaped sheath in order to facilitate the cyclical motion as the muscle alternatively contracts and relaxes. Preferably, the polyurethane cone-shaped piece is to be made from a material, such as that described in U.S. Pat. Nos. 4,675,361 and 4,689,383, incorporated herein by reference. The material should simultaneously, be compatible with surrounding tissues, have a low coefficient of friction, and be stable when implanted in-vivo for long periods. The weight of the convertor 130 is estimated at about 18 gms with fluid.

Figure 23:
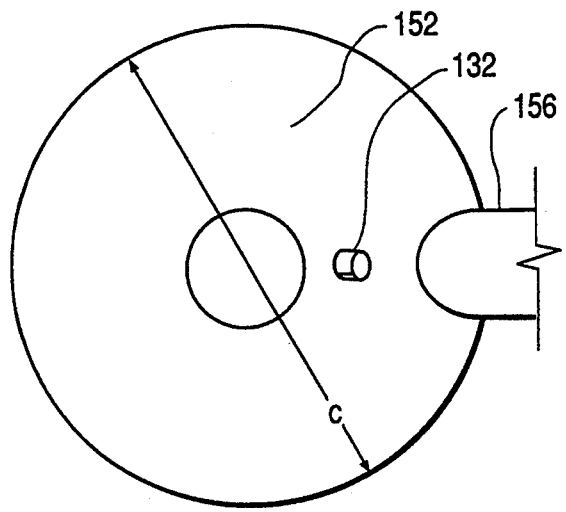
FIG. 23 is a top plan view of the two-stage hydraulic actuator of FIG. 21.
Figure 24:
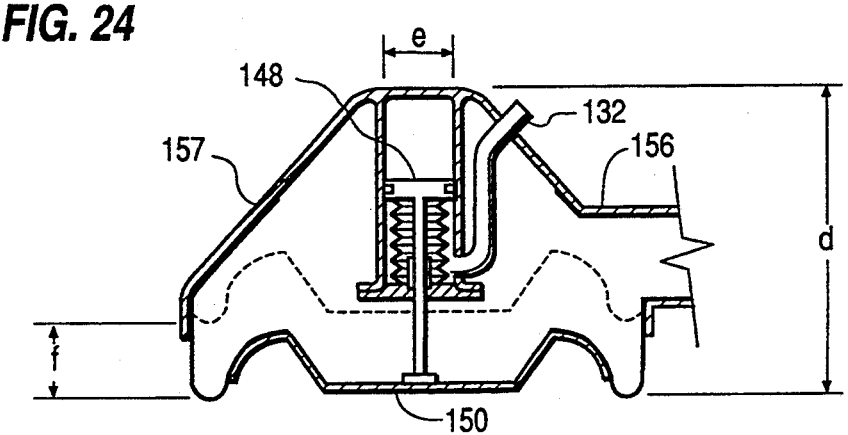
FIG. 24 is a cross-sectional view of the two-stage hydraulic actuator shown in FIG. 23.
Figure 25:
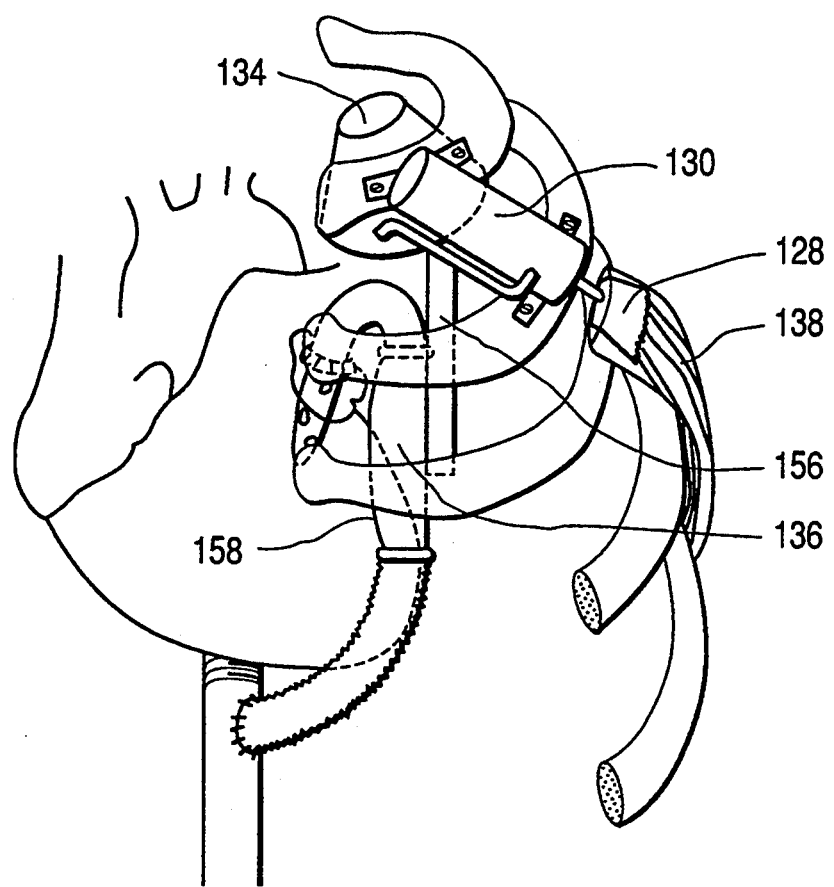
FIG. 25 illustrates another preferred embodiment of the skeletal muscle energy conversion system as implanted.

The two-stage hydraulic actuator 134 in which the hydraulic pressure is reduced from a high pressure of approximately 100 psi to 2 psi, or near physiological pressure, by an increase in displacement, and to which the transmission line 132 from the convertor 130 connects, is mounted inside the thoracic cavity. Similar to the convertor 130, it is also firmly affixed to the skeleture as described below. The preferred embodiment of a cone-shaped actuator 134 is shown in FIGS. 23 and 24. The actuator 134 has a diameter "c" of approximately 7.6 cm, a height "d" of approximately 5.0 cm at its center when expanded, and an estimated dry weight is about 45 gms, while its total weight with hydraulic fluid is about 180 gms. High pressure hydraulic fluid at approximately 80-200 psi is received from the high pressure hydraulic transmission line of the convertor 130 and causes the center piston 148 having a diameter "e" of approximately 1.1 cm to move with a displacement of about 1.4 ml. This in turn causes the larger piston 150 at the skirt 152 of the actuator 134 to move with the same stroke length "f" as the center piston which is about 1.4 cm. However, since piston 150 has an area that is generally 50 times larger than the center piston 148, it causes a displacement of up to 70 ml at physiological pressure. The exact stepdown ratio will be easily optimized by those skilled in the art. This low pressure hydraulic fluid chamber 154 is connected via a low pressure hydraulic line 156 to an implanted medical device 136, such as a VAD 158 implanted in an atrial aortic shunt as shown in FIG. 25. The low pressure hydraulic line 156 is a large diameter (1.8 cm) flexible tube that is about 5 cm long. This tube is wire reinforced to provide low compliance to the hydraulic fluid with good bending flexibility. The close coupling through a short but large diameter tube minimizes fluid flow losses. Since in this embodiment the hydraulic fluid cycles in syncrony with the heart, the VAD thus augments the cardiac output.

An additional feature which will need to be considered for implantation is fluid reservoirs for the hydraulic fluid. Since the high pressure and low pressure fluid systems use the same type of fluid, it may be possible to have only one reservoir with pressure equilization valves to each separate hydraulic space.

Figure 26:
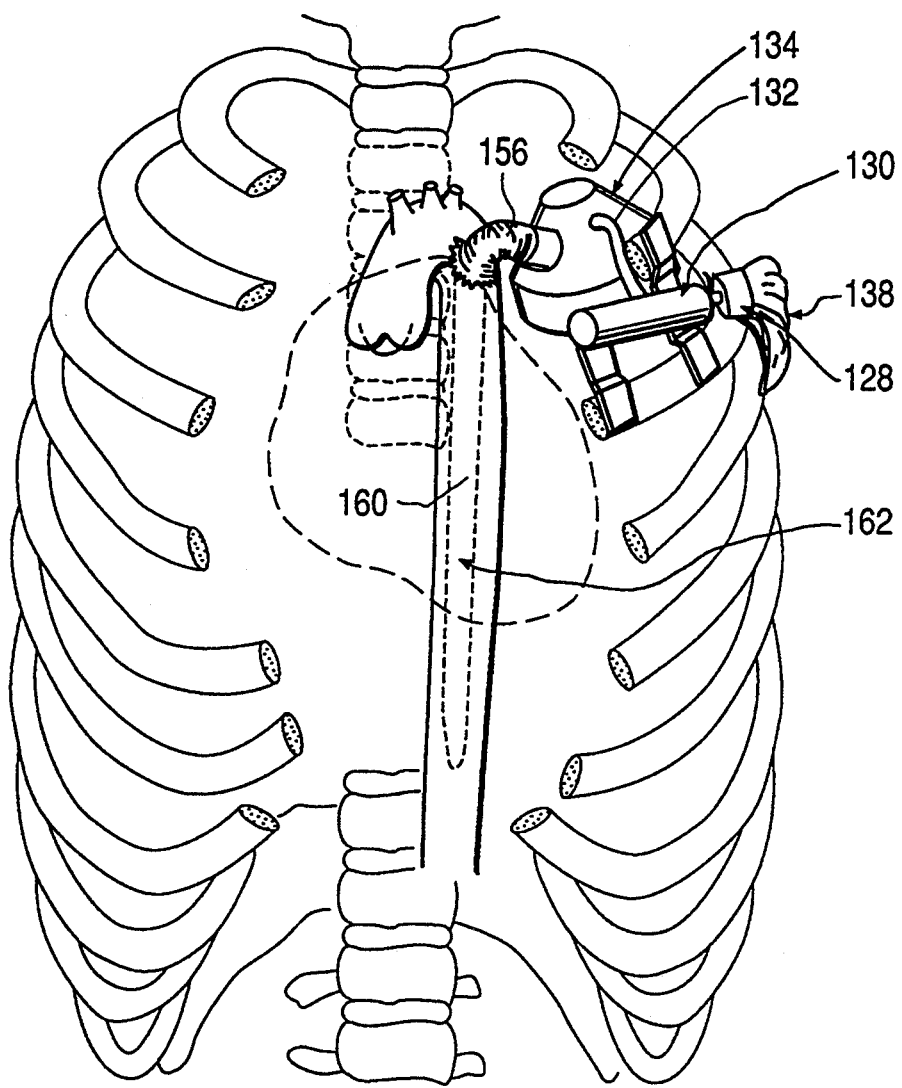
FIG. 26 illustrates another preferred embodiment of the skeletal muscle energy conversion system as implanted.

As shown in FIG. 26, the cone-shaped actuator 134 is designed to fit in the left apex of the pleural space above the left lung, in close proximity to the circulatory support device 16 which it drives and the convertor 130 which drives it. The actuator 134 is also encapsulated in polyurethane in the same way and for the same purposes as the convertor 130. In this instance, the circulatory support device 160 is an intraaortic balloon 162 implanted below the actuator in the aorta.

Preferably, as illustrated in FIG. 21, the present invention also provides the option of operating the hydraulic system externally, by connecting a percutaneous cuff 166 to the high pressure hydraulic line 132 via a small diameter tube 168 and an access port 164. As discussed below, this may be required temporarily after system implantation, for external actuation during muscle training, or for emergency backup use. Another important benefit provided by the access port is the adjustment of skeletal muscle pre-stretch. During blood pump deflation the latissimus dorsi, or other muscle, should be stretched to near optimal pre-stretch for the next beat in order to improve system performance. Starling's Law suggests that maximum energy output will be obtained from pre-stretched muscle. By adjusting the volume of fluid in the high pressure hydraulic system after implantation of the energy convertor and attachment of the muscle, the degree of muscle pre-stretch can be controlled. The access port provides for this volume adjustment.

Figure 27:
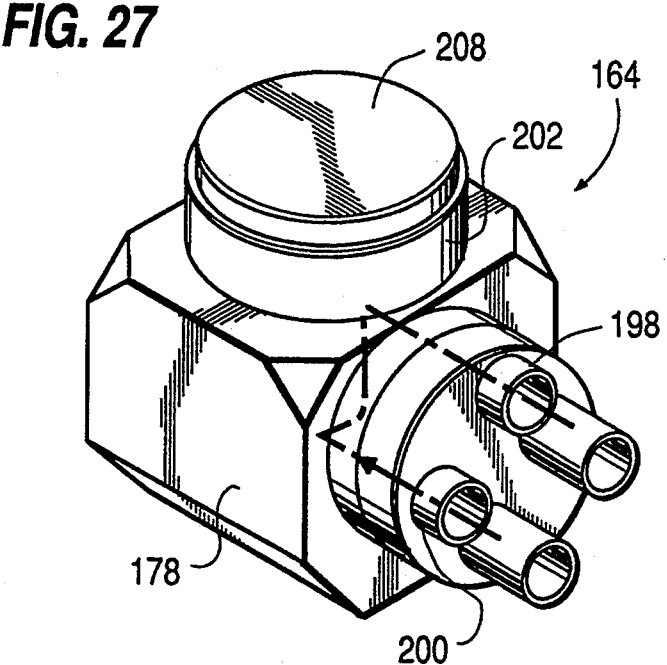
FIG. 27 is a perspective view of the access port of the present invention in a first position.
Figure 28:
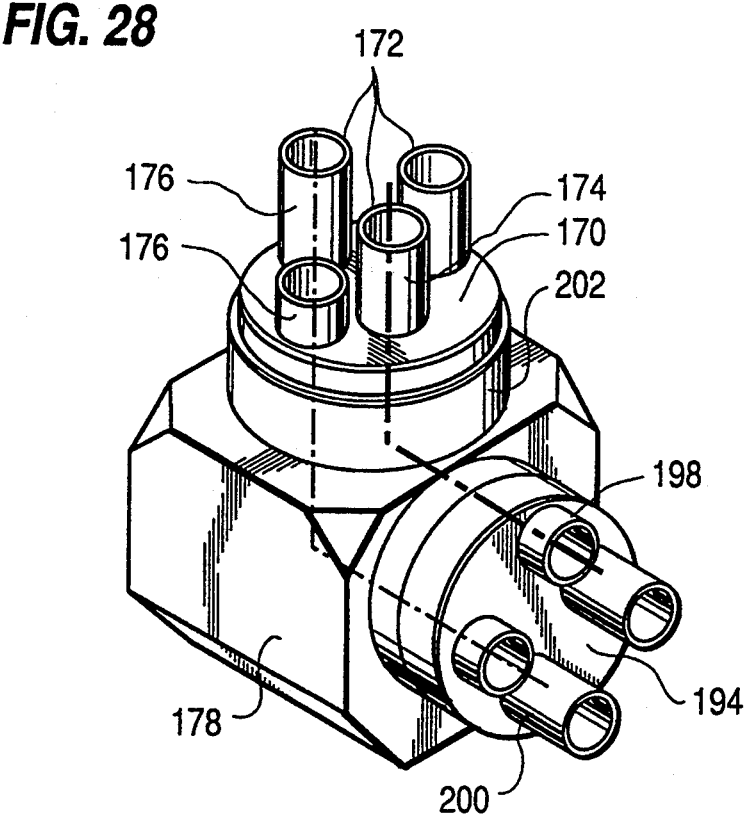

Referring back to FIG. 21 again, the access port 164 is inserted in the high pressure hydraulic transmission line 132 interconnecting the hydraulic convertor 130 and the hydraulic actuator 134 which powers the implanted medical device 136 or blood pump. The access port may also be a site for transcutaneous or percutaneous telemetry to monitor the functioning of the skeletal muscle energy conversion system. Operation of the access port 164 can best be understood by referring to FIGS. 27 and 28, which show the access port 164 in its two modes of operation. FIG. 27 shows the access port 164 as it would be set once the training and conditioning and training is complete, and the skeletal muscle is powering the blood pump(s). In this situation, high pressure hydraulic fluid coming from the convertor 130 is shunted directly to the blood pump(s) and a sealing cap 208 is in place on the housing 178. Since the energy conversion system is capable of powering two blood pumping devices (for biventricular support), there are two sets of ports 196 shown. FIG. 28 shows the access port 164 as it would be set up at the time of implantation. A housing end cap 170 with ports 172 that connect through percutaneous tubes to an external console would be in place. In this case, the high pressure hydraulic fluid from the hydraulic convertor 130 is shunted through these external ports 172 and tubes to a variable hydraulic load with instrumentation to monitor output. The other two tubes and ports will connect hydraulic pumps located in the external console with the hydraulic actuator operating the blood pumps, or other devices.

The relative size of the access port 164 is roughly a one inch cube. The external surfaces are covered with a velour or porous mesh designed to promote the ingrowth of tissue, thus eliminating a sinus tract or volume in which fluids could otherwise accumulate, predisposing to infection. All of the ports 172 and 196 are hydraulic-type ports operating with a suitable hydraulic fluid such as silicon fluid, isotonic physiologic fluid, or similar low viscosity hydraulic fluid. Since any fluid loss would have severe consequences, these access ports are all of a secure and sealed type. The entire access port 164 is to be implanted in a shallow subcutaneous pocket, which can be either fitted with percutaneous lines to or from the ports 172, but at other times be buried under the skin so as to avoid risks of infection. The access port 164 must permit quick access in the event of a medical emergency, allowing the patient to be connected to an external hydraulic drive console either outside the hospital, in the ambulance, in the emergency room, in an intensive care facility, or in the operating room.

Port 174 on housing end cap 170 would typically be interconnected to an external hydraulic dynamometer used to apply a controlled and measurable load on the hydraulic actuator. This would allow the assessment of the capabilities of the skeletal muscle to power the blood pump(s) during the initial healing-in. Port 176 on housing end cap 170 would typically be interconnected to an external hydraulic pumping means in order to allow hydraulic actuation of the implanted medical device or blood pump(s) when the skeletal muscle contractile energy is not being utilized.

Since the present energy conversion system is designed to actuate either a LVAD, RVAD, or Bi-VAD, the ports 172 and 196 will all have two separate parallel fittings and lines. This permits the simultaneous but independent actuation of both an LVAD and RVAD (thus a Bi-VAD). It is also possible that a Bi-VAD may be driven from either the same hydraulic actuator or separate hydraulic actuators.

Due to the need for a secure system, and considering the corrosive nature of the body fluids, the access port 164 is made with titanium, stainless steel, an engineering polymer, or other physiologically compatible material.

Figure 32:
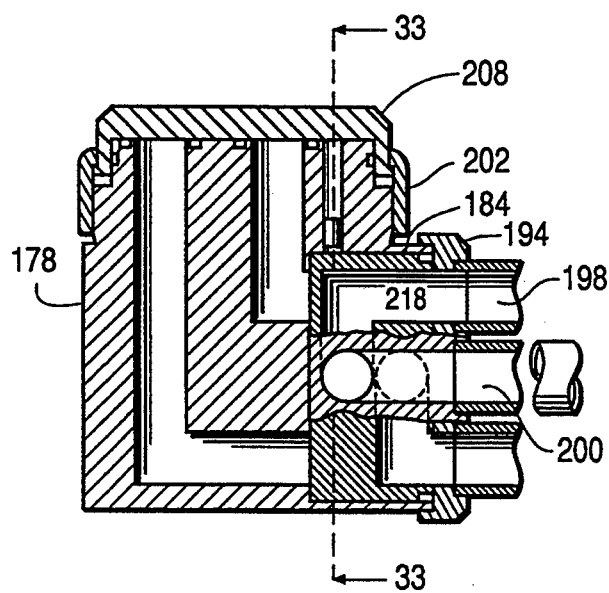
FIG. 32 is a cross-sectional view of the access port shown in FIG. 27 taken generally along the line 32—32 of FIG. 33.
Figure 33:
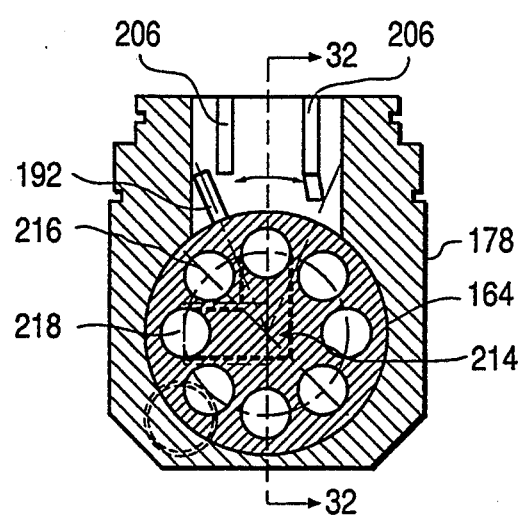
FIG. 33 is a cross-sectional view of the access port of FIG. 27 taken generally along line 33—33 of FIG. 32.
Figure 34:
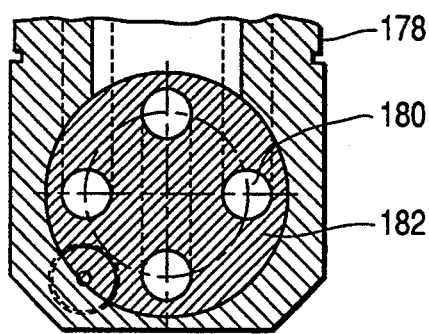
FIG. 34 is a partial cross-sectional view of the access port of FIG. 33 with a part thereof removed.

Referring to FIGS. 29-34, the internal details of the preferred access port 164 are illustrated. The main block or housing 178 of the access port 164 is shown in FIG. 34 with several fluid passages 180 drilled out and with a cylindrical recess 182 in one side thereof. A right circular cylinder 184 having two parallel flat surfaces 186 and 188 is disposed within recess 182 and has surfaces 186 and 188 lapped flat so as to permit easy rotation within the block 178, yet allow very little leakage between adjacent passages 180 terminating at the flat surfaces of the cylinder. A retaining ring 202 that secures the housing end cap 170 in position on the housing 178 is also provided. The cylinder 184 also includes a plurality of first and second fluid passages 218 and 216, respectively. A ball-detent mechanism 190 to hold the rotation within the housing 178 in either of the two possible positions described above is also provided. The cylinder 184 is rotated by a side-arm post 192, which is visible and accessible when the housing cap 170 is not in place.

As illustrated, side-arm post 192 is rotatable within a groove 204 formed in housing 178. Additionally, rotation stops 206 project downwards from the under side of housing end cap 170 or housing sealing cap 208 so as to ensure post 192 and thus cylinder 184 remain in the proper position.

Figure 29:
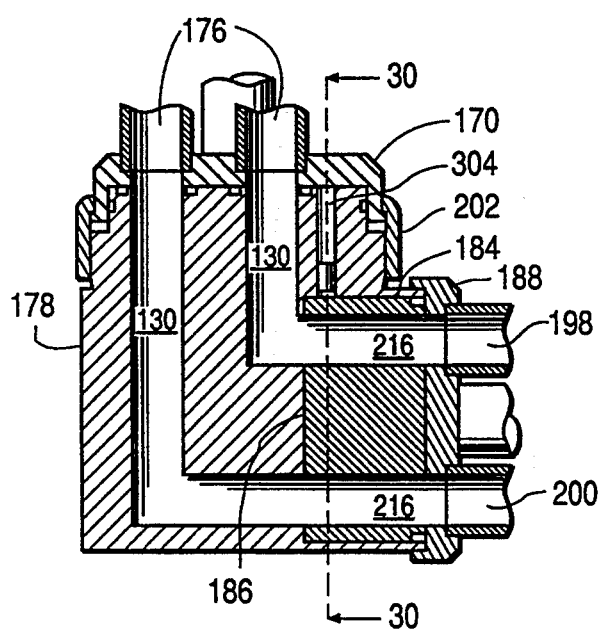
FIG. 29 is a cross-sectional view of the access port of FIG. 28 taken generally along the line 29—29 of FIG. 30.
Figure 30:
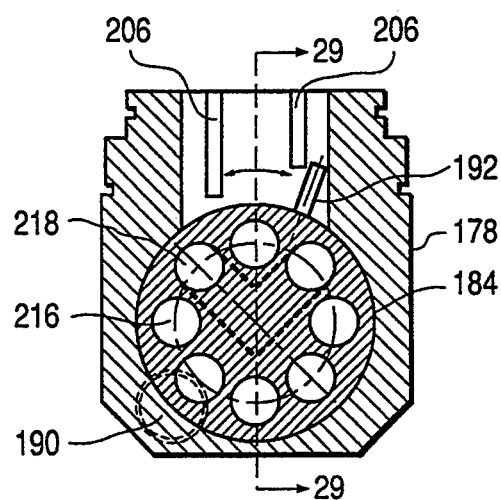
FIG. 30 is a cross-sectional view of the access port of FIG. 28 taken generally along the line 30—30 of FIG. 29.
Figure 31:
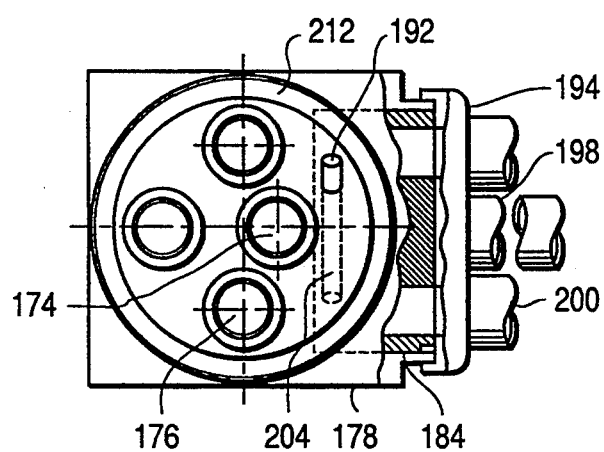
FIG. 31 is a top plan view of the access port shown in FIG. 29 with a portion thereof removed.

A cylinder cap 194 with ports 196, each about ⅛" diameter, is designed to be left in place at all times once the access port 164 is assembled at the time of manufacture. With the cylinder 184 in the first position shown in FIG. 27, fluid entering port 198 would be connected internally to port 200. As illustrated in FIGS. 32 and 33, first fluid passage 218 forms an internal passageway 214 within cylinder 184. Thus, when cylinder 184 is in the first position, first fluid passage 218 is aligned with ports 198 and 200 such that fluid entering port 198 will exit port 200, and vice versa. Internal passageway 214 includes three right angle elbows in order to effect the reversal of the fluid direction. With the cylinder in the second position shown in FIG. 28, port 198 will be connected to port 174, and port 200 will be interconnected to port 176. As illustrated in FIGS. 29 and 30, when cylinder 184 is in the second position, second fluid passages 216 are aligned with ports 198 and 200, and second fluid passages 216 are in communication with housing passages 180. Thus, fluid entering port 198 will exit port 174, or vice versa, and fluid entering port 200 will exit port 176, or vice versa.

At the time of surgical implantation, ports 172 and housing end cap 170 will be used, and the cylinder 184 will be in the second position. When muscle training and conditioning is completed and it has been demonstrated that the skeletal muscle is capable of powering the blood pump(s), the cap 170 will be removed so that side-arm post 192 is accessible, the side-arm post 192 will be moved to the first position, and a housing sealing cap 208 without the ports 172 will be installed on the housing 178 with a retainer ring 202. An "O" ring 210 within the O-ring groove 212 prevents leakage to the external environment. After securing the cap 208 in place, and after determining that the skeletal muscle energy conversion system is operating properly with good circulation of the patient's blood, the access port 264 will usually be closed surgically in a subcutaneous pocket. It will be apparent to those skilled in the art that the access port 164 described herein can be utilized with any embodiment of the present invention in which the transmutable energy is transmitted via hydraulic fluid. Further, although described in connection with the energy conversion system of the present invention, it should also be apparent that the dual access port described herein can be utilized with a variety of other implantable circulatory support devices.

In designing the energy conversion system using high pressure hydraulic transmission, various components of the convertor and two-stage actuator require fluid seals that prevent gain or loss of hydraulic fluid. One approach is a metallic membrane such as a metal bellows that can be used to prevent diffusion of liquids while allowing motion between components. Alternatively, a polymer membrane such as a rolling diaphragm or the blood-contacting element of the blood pump can be used and net gain or loss or fluid can be prevented by keeping all fluids in osmotic equilibrium. Another approach would be using polymer membranes which can be used with fluids such as silicone oils that are not miscible in body fluids and which diffuse extremely slowly through certain polymer materials. An "imperfect seal," such as a sliding polymer piston ring, should be used if fluid only leaks from one internal space to another internal space and a mechanism is available to return the fluids to their proper chambers or reservoirs, thus maintaining steady-state conditions.

As illustrated in FIG. 22, welded metal bellows 146 seals the piston shaft 140 of the convertor 130. A welded bellows is used to minimize compressed length and the bellows is fabricated of unalloyed titanium for corrosion resistance and to minimize the spring rate of the bellows assembly. The convertor piston 142 uses a piston ring 141, since fluid leaks only from one hydraulic space to another. Similar piston seals are used on the high pressure portion of the hydraulic actuator.

Referring to FIG. 17, the low pressure piston 122 of the hydraulic actuator 126 is sealed by a rolling diaphragm 123 which would preferably be made from the polyurethane material taught in U.S. Pat. Nos. 4,675,361 and 4,689,383, which is the same material used for the blood pump.

The above-described skeletal muscle powered linear energy conversion system is a versatile system able to drive a variety of different blood pumps to meet the need of the full range of patients requiring mechanical circulatory support. The specific energy convertor and actuator modules, stimulators, and attachment systems, can be selected by those skilled in the art for the specific requirements of counterpulsation devices or prosthetic ventricles. Table 3 below shows examples of possible blood pump types that may be powered with this energy source, including intraaortic balloon pumps, parallel or single-port aortic counterpulsation devices, intraventricular balloon pumps, ventricular assist devices (right, left, or biventricular), and artificial hearts. Each of these devices is discussed briefly below.

In comparing these two main approaches, counterpulsation vs. prosthetic ventricle (Table 2), certain tradeoffs become apparent. Counterpulsation with passive deflation is the simplest of all the approaches and has the lowest power consumption. However, it also provides the least circulatory assistance due to less afterload reduction than with other approaches. An improvement can be realized by the use of counterpulsation with augmented deflation, which provides greater left ventricular pressure reduction due to improved muscle preloading, but at approximately a 40% increase in power. A prosthetic ventricle provides the maximum circulatory support but again requires the most power (about 2.3 times as much as counterpulsation with passive deflation).

The principles of counterpulsation are well established, and present day pneumatic intraaortic balloon (IAB) pumps are an accepted part of most cardiac surgical programs. An optimally timed IAB in counterpulsation with the natural heart provides cardiac assistance with two benefits, namely, systolic afterload reduction and diastolic augmentation of coronary perfusion pressure. These two effects in turn reduce subendocardial ischemia and reduce anginal pain. Depending on the cardiac pathophysiology of an individual patient, IABs can reduce the work of the heart and increase cardiac output by 10 to 20%. This can be a significant advantage to CHF patients who have exhausted their cardiac reserve. The stroke work requirements of intraaortic balloon counterpulsation is approximately 0.75 joules per stroke (see Table 1).

TABLE 1

| Options with Skeletal Muscle Power | |
| --- | --- |
| Stroke | Work |
| Counterpulsation IAB assistance | 0.75 joule |
| Prosthetic Left Ventricle Valved blood pump Intraventricular balloon | 1.75 joules |

On the other hand, devices categorized as prosthetic ventricles (ventricular assist devices, artificial heart ventricles, intraventricular ventricular balloon pump) can take over the complete work of the heart or ventricle by receiving blood directly from the venous return and pumping it into the arterial system. Present day prosthetic ventricles have been shown to be enormously effective in sustaining the pulmonary and/or systemic circulation, even in patients who are in chronic ventricular fibrillation and thus have no biologic cardiac output. Prosthetic ventricles provide more circulatory support than counterpulsation devices, but as shown in Table 2, the compromise is greater power requirements (stroke work estimated at 1.75 joules) and more complexity due to the necessity of having prosthetic heart valves in the pump. However, there is one exception, the intraventricular balloon pump, which is described below.

TABLE 2

| Counterpulsation vs. Prosthetic Ventricle | | |
| --- | --- | --- |
| Approach | Advantages | Disadvantages |
| 1. Counterpulsation with passive deflation | Low power required | Minimum left ventricular pressure reduction. |
| 2. Counterpulsation with augmented deflation | Faster deflation (more left ventricular pressure reduction) Improved muscle preload | 40% more power required. |
| 3. Prosthetic ventricle | Maximum circulatory support | 130% more power required than #1 above |

TABLE 3

| Blood Pump Alternative Approaches | |
| --- | --- |
| Counterpulsation | |
| 1. | Intraaortic balloon pump |
| 2. | Valveless aortic counterpulsation pump |
| 3. | Parallel extraaortic balloon pump |
| Prosthetic Ventricles | |
| 4. | Intraventricular balloon pump |
| 5. | Ventricular Assist Device |
| 6. | Total artificial heart (or bilateral prosthetic ventricles) |
| Other | |
| 7. | Right or left ventricular pusher device |

Referring to Table 3, Intraaortic Balloon Pump (IAB) patients include patients in New York Heart Association (NYHA) Class "III-$\frac{1}{2}$", or patients in between Classes III and IV. These are patients who are too well to qualify for transplantation but have symptoms of fatigue, dyspnea, and anginal pain with minimal physical exertion. The IAB approach will also do well for patients for whom medical and surgical therapy have failed to relieve angina, or for patients who require long-term arrhythmia control. The technical problems to be encountered with an IAB are fairly predictable and the surgical procedures require no new development. With an intraaortic balloon in the thoracic aorta, as shown in FIG. 26, there is also less risk associated with deactivation, should that be required for muscle training or for muscle resting. One negative is that little is known about chronic IABs in cardiomyopathy patients with congestive heart failure. The magnitude of hemodynamic improvement is unknown in this subgroup compared to good data available for patients requiring anginal or arrhythmia control. However, a closely-coupled hydraulically actuated IAB should be more effective than a loosely-coupled pneumatically actuated IAB upon which most clinical data is based.

Figure 35:
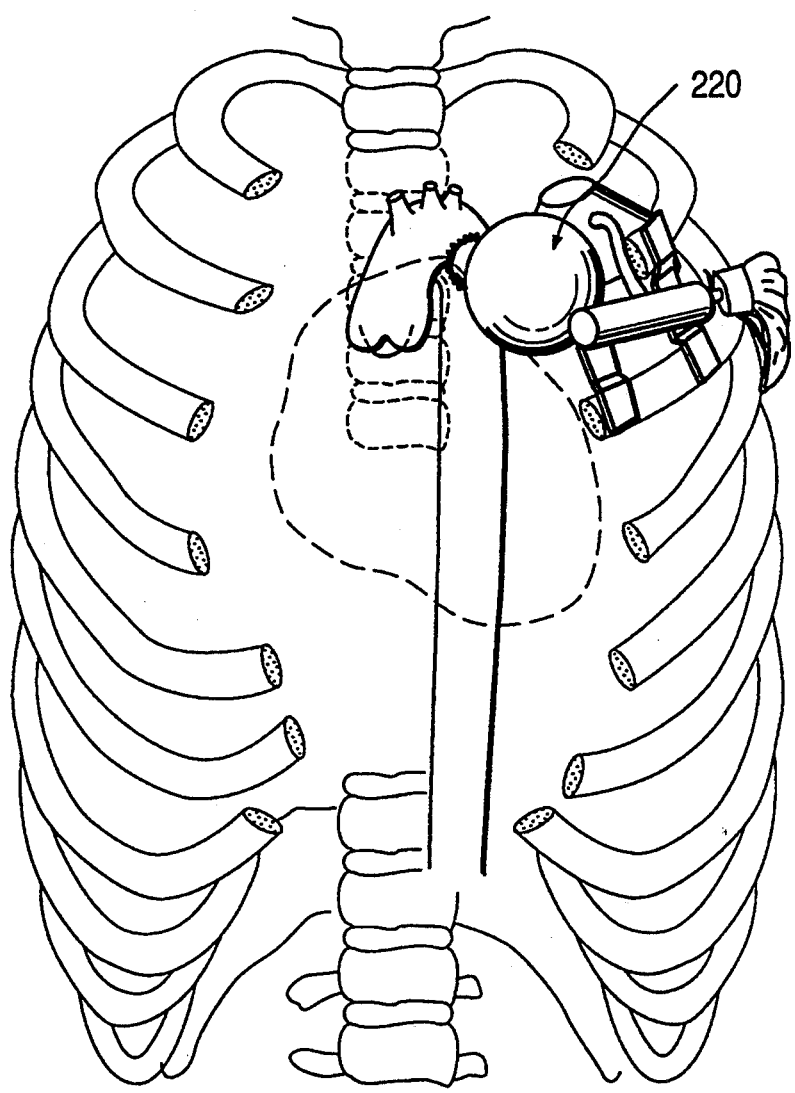
FIG. 35 illustrates the preferred embodiment of the skeletal muscle energy conversion system utilized with a valveless counterpulsation pump.

Also listed in Table 3, the valveless counterpulsation pump is one device that has been proposed, but that has not yet been used clinically. This valveless counterpulsation pump 220, as illustrated in FIG. 35, essentially functions as a super intraaortic balloon. It can have a larger stroke volume than an IAB and provides more assistance than the traditional IAB. The configuration is similar to a ventricular assist device but it has only one port which is sutured to the aorta and has no valves. Blood is drawn into the chamber during cardiac systole and ejected into the aorta during cardiac diastole. Possible disadvantages include the unknown clotting potential of this configuration, particularly in the event of reduced pumping or a "pump-off" situation. Also, the extraaortic placement means more intrathoracic space required for hardware.

Figure 41:
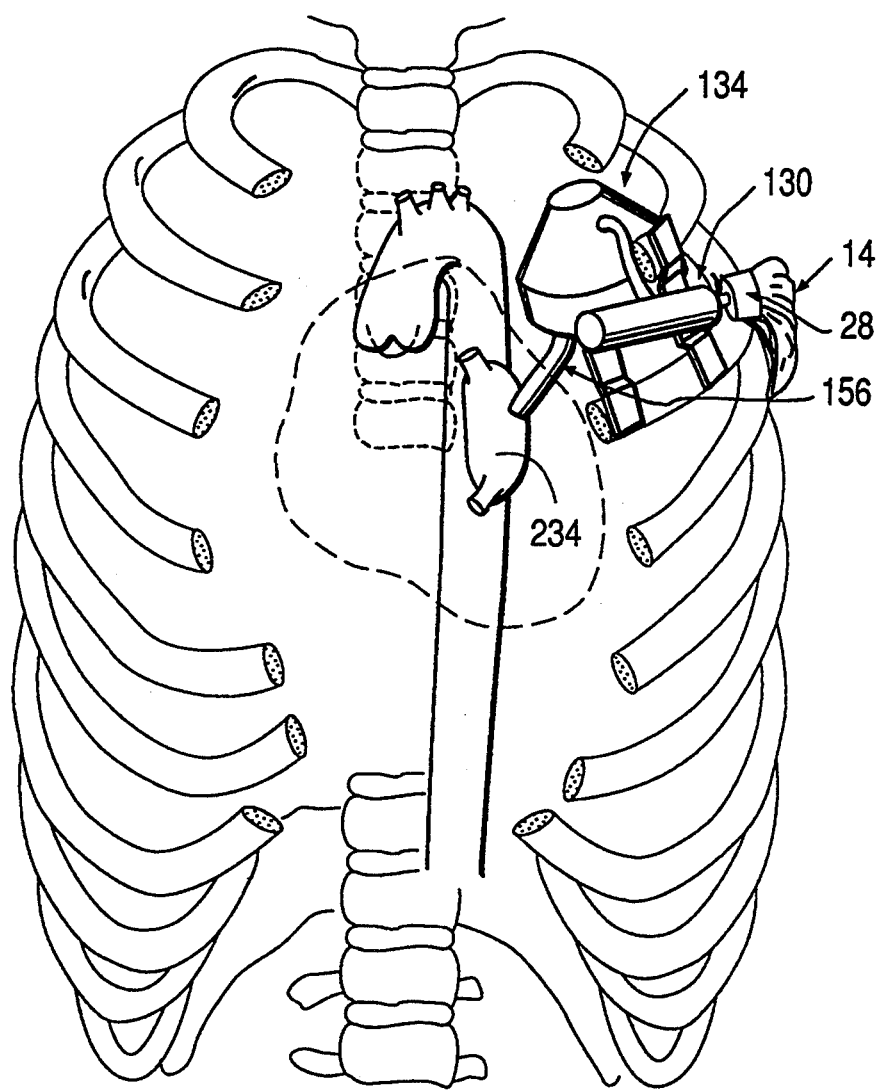
FIG. 41 is a schematic illustration of the preferred embodiment of the skeletal muscle energy conversion system operating a parallel extraaortic balloon pump.
Figure 42D:
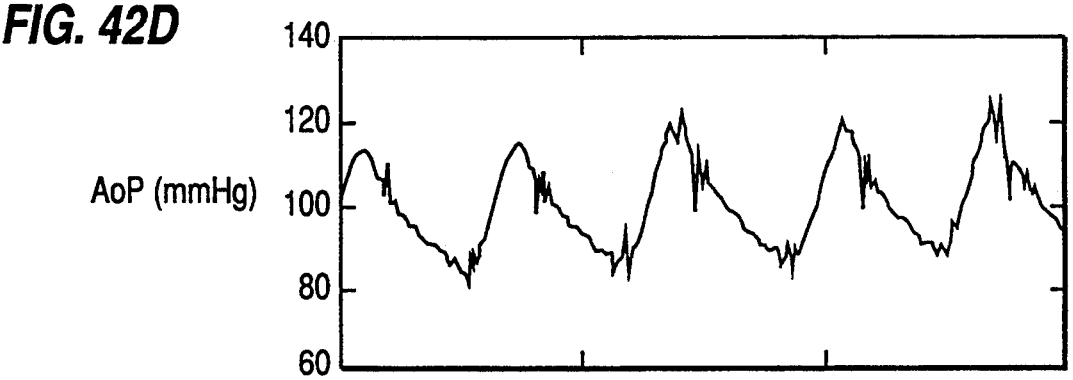
FIGS. 42A–D is a graphic representation of the results over rime or operating an engineering model of a VAD powered by skeletal muscle, including muscle displacement (A), hydraulic pressure (B), circulatory flow (C) and circulatory pressure (D).
Figure 42C:
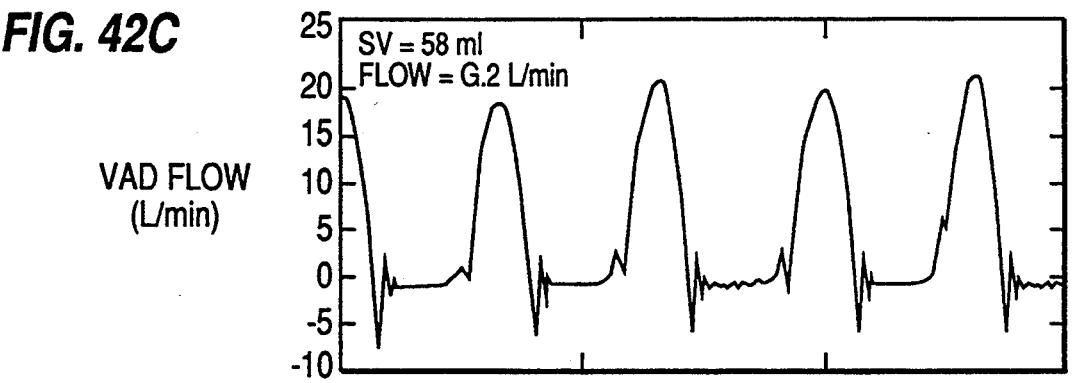
Figure 42B:
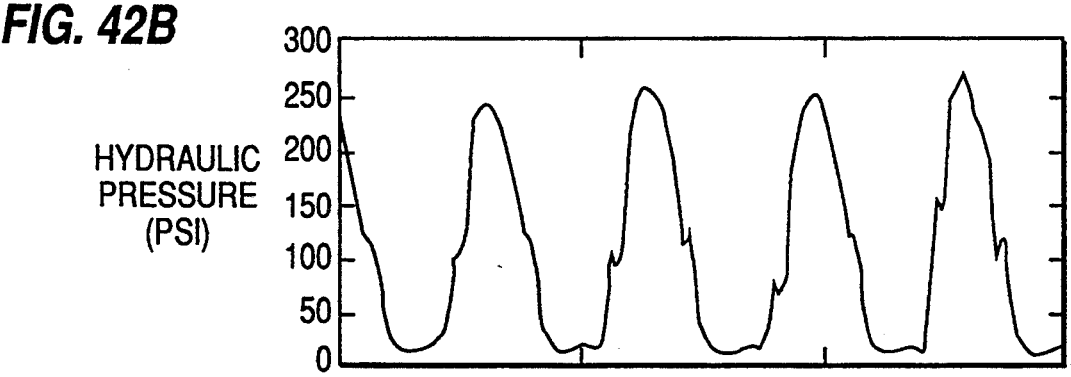
Figure 42A:
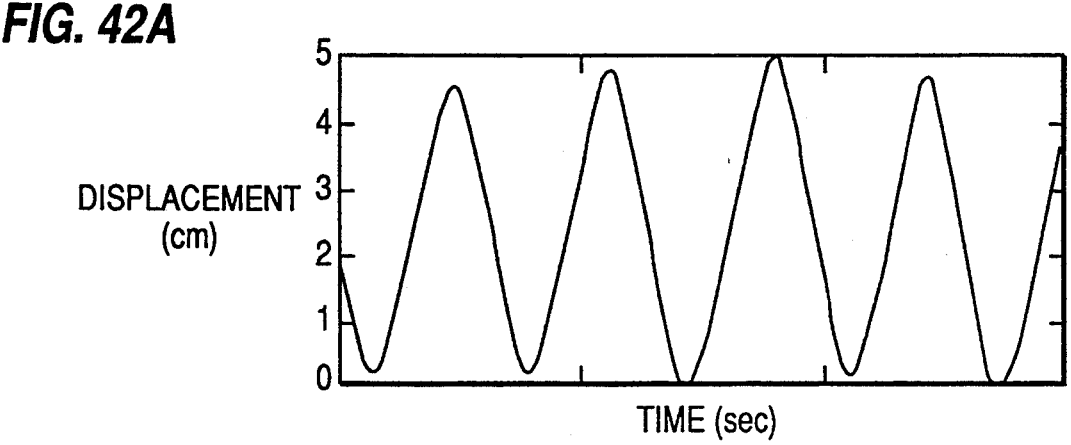

The parallel extraaortic balloon pump 234, as shown in FIG. 41 connected to a preferred embodiment of the skeletal muscle energy conversion system described herein, is another type of counterpulsation device which is connected at two sites to the descending thoracic aorta. The advantage of this device is that it eliminates a prosthetic balloon inside the aorta, but this parallel approach requires more extensive surgery and more intrathoracic space for the device. Also, there is some increased thromboembolic risk due to its parallel nature, resulting in a lower blood velocity in each path. To increase flow velocity through the blood pump, some investigators have proposed ligation of the aorta, but that in turn has its own thromboembolic risk due to stasis at the ligation site.

Figure 40:
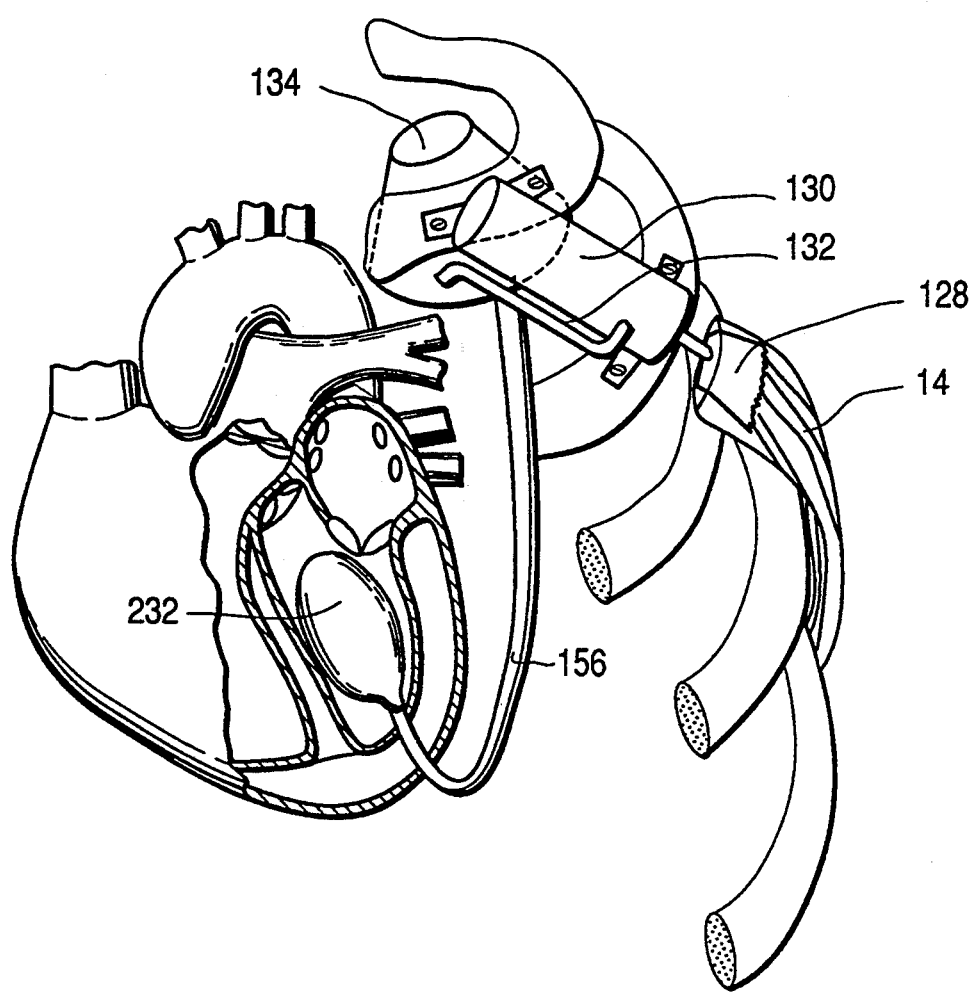
FIG. 40 is a schematic illustration of the preferred embodiment of the skeletal muscle energy conversion system operating an intraventricular balloon pump.

The intraventricular balloon pump listed in Table 3 produces a net forward flow of blood. As shown in FIG. 40 connected to a preferred embodiment of the skeletal muscle energy conversion system, the intraventricular balloon pump 232 is inserted through the ventricular apex and is inflated to assist the ejection of blood during cardiac systole. This device would therefore not be in counterpulsation but in synchrony with the biologic heart, deflating in diastole and inflating in systole. It could perform a large part of the work of the heart by ejecting each stroke volume during natural heart contraction. One main advantage of this approach is that it can produce forward blood flow without any prosthetic valves, and therefore is relatively simple in design. However, one disadvantage is the unknown effect of device fixation at the ventricular apex on ventricular function. Although this would probably have little affect in normal hearts, loss of the apical contribution to left ventricular ejection may be detrimental in patients with certain cardiac pathologies. As long as there was no disruption in prosthetic pump function, this may be of no consequence; but if it is desirable to periodically turn off the device, this could have some negative affect on cardiac performance. Also, it is not known how well this device would perform in patients with extremely dilated ventricles.

The ventricular assist devices and artificial hearts listed in Table 3 are prosthetic ventricles complete with inflow and outflow valves. Therefore, although they are the most complex of any support device, they also provide the most complete circulatory support. Univentricular and biventricular VADs can be very effective in providing total circulatory support. Patients are best treated with prosthetic ventricles. The greater power possible with a prosthetic ventricle makes it best suited as the chronic system to be used in lieu of heart transplantation.

Finally, another type of device that is worthy of note is the ventricular pusher device, which may be a hydraulic chamber that attaches to the anterior rib cage or a hydraulic chamber surrounding the heart and enclosed in a hard shell as described in U.S. Pat. No. 4,690,134 which is inflated by the skeletal muscle energy conversion system to push on the ventricular wall. One advantage is that the system does not touch blood directly and therefore is safe from thromboembolism. However, one drawback is that it is probably useful mainly for right ventricular assistance, and therefore might only meet the clinical need of a limited group of patients. Alternatively, this device could be sutured directly to the ventricular wall, and could thus assist either side of the heart.

Figure 36:
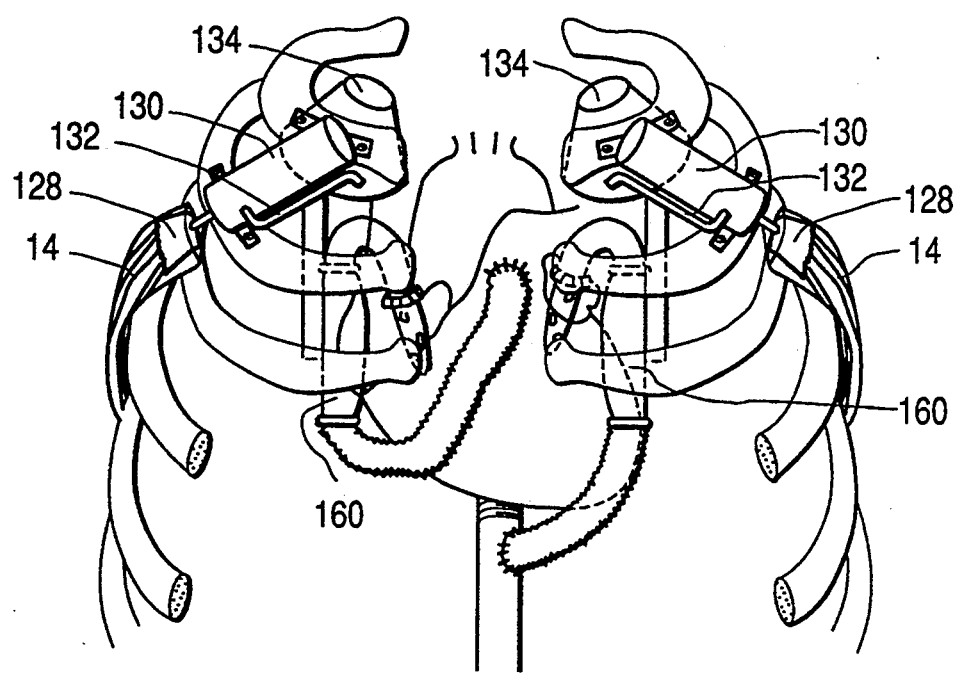
FIG. 36 is a schematic illustration of dual energy conversion systems of the present invention operating biventricular assist devices.

The reliability of medical devices is always important, but particularly so with a life-sustaining device. One way to achieve increased reliability is through redundancy. Referring to FIG. 36, the skeletal muscle energy conversion system of the present invention can be set up as a redundant system having muscle-actuation systems on both the left and the right sides of the heart, each connected to one of the above circulatory support devices at the hydraulic step-down actuators via high pressure hydraulic lines, thereby forming a Bi-VAD system.

There is a latissimus dorsi muscle on both sides of the human body. Therefore, it is possible to provide a skeletal muscle actuation system symmetrically on both sides of the body. Each side of the dual system would include the muscle 14, muscle attachment means 128, a hydraulic convertor 130, a hydraulic actuator 134, muscle stimulator means (not shown), and related accessories. Hydraulic lines 132 from each convertor 130 would be connected to the hydraulic actuator 134 for each blood pump or other circulatory support device 160.

Thus, redundancy for increased reliability would be at the expense of an increase in the cost, in the size, and in the weight of implanted components, and it would involve expanded surgical implantation. Thus, it is important to note that redundancy is included in the overall evaluation of the present invention, yet it is considered an optional feature, as opposed to a mandatory one. Redundancy should not be added as a required feature unless the advantages are worth the added cost and complexity.

Alternative to a Bi-VAD, dual energy conversion systems can also be attached to a single circulatory support device, such as a left ventricular assist device (LVAD) which drives only one blood pump. A crossover in the high pressure hydraulic system could be provided such that if either side failed, the functioning side would continue to drive the blood pump.

Surgical Installation

Surgical installation of the implantable skeletal muscle energy converting device involves firmly attaching the energy converter to the body, as well as detaching one end of a skeletal muscle from its site of attachment to a bone and connecting the end of the muscle to the movable part of the energy converting device, e.g., piston shaft 140 of convertor 130 in the preferred embodiment shown in FIG. 36. Anatomical and mechanical considerations described below will govern the selection of attachment sites and muscles used in the installation, and the selection can be made by those skilled in the art in view of these considerations.

In order to harness the skeletal muscle for use in driving a medical device, contraction of the muscle must be stimulated according to the needs of the medical device.

Muscle stimulators have been described elsewhere by others for training and fatigue-resistant pacing protocols (see, e.g., U.S. Pat. No. 4,411,268 assigned to Medtronic, Inc., and incorporated herein by reference), and are within the skill of the ordinary worker. If counterpulsation assist is desired, two sets of pacing wires will be needed, one for the heart and one for the skeletal muscle, so that they can be operated synchronously. A stimulator with only a pacing lead to the muscle could be designed using a ventricular assist device with asynchronous pumping, which has been shown to be quite effective in current clinical trials (Farrar, et al. (1990), *J. Heart Trans.*, 9:415–423).

A review of the literature shows the basic feasibility of both neural and direct muscle stimulation. Based on this literature, it appears that neural stimulation is best provided by a cuff-type neural electrode, while direct muscle stimulation is best achieved with an intramuscular wire electrode.

Effective pacing can be realized by stimulating at 10 Hz with a neural cuff-type electrode and a 4 to 5 volt amplitude, probably synchronized with the natural heart. Details in regard to pulse-width, the input impedance looking into the muscle system, and other characteristics of the pulse train are generally in the literature, and the particular electric stimuli desired can be easily obtained by those skilled in the art. This is also true in regard to the conditioning of skeletal muscle, or regimens for transforming it.

Selection of Attachment Sites

The object of this invention is to maximize the power captured from a skeletal muscle for use by prosthetic devices. To maximize the force generated by the muscle, the skeletal muscle energy converting device should be firmly attached to the skeleton, so that none of the contraction is dissipated in moving the converter. The preferred location for attachment of the converter is the rib cage. An attachment site on the rib cage is particularly preferred if the energy converting device is to provide power for circulatory assist devices, because such a location will also place the energy converting device near the heart, resulting in minimum distance for transmission of energy and minimum energy loses due to transmission.

The muscle selected for attachment to the skeletal muscle energy convertor must be capable of generating sufficient power to drive the implanted device, so the size of the muscle must be considered in the selection. As disclosed above, the power available from skeletal muscle has been estimated to be from 3 to 15 mW per gram muscle, and the muscle selected should have sufficient size to produce the power requirements of the device it is intended to drive.

The skeletal muscle energy conversion device is preferably placed in substantially linear alignment with the muscle, so that the muscle contraction moves the movable part of the energy converter in the same direction that the muscle pulled before being attached to the energy converter. The muscle can be expected to generate the maximum force by pulling in this orientation. If the converter is attached to the rib cage, then the preferred muscle for powering the skeletal muscle energy converting device is one of the muscles in close proximity to the thoracic cavity. Particularly preferred muscles include the latissimus dorsi, the rectus abdominis, the psoas major. All of these muscles have either an origin or insertion that is near the rib cage, and thus, one end of the muscle may be detached from its connection to bone and attached to the converter while leaving the muscle substantially in situ. Substantially in situ, as used herein, means at least one end of the muscle remains attached to its natural origin or insertion, and most of the muscle is unmoved from its normal anatomical position, with the majority of the blood supply to the muscle remaining intact. The natural neural connections may also be left intact if the muscle is to be stimulated by a cuff-type electrode, or the muscle may be ennervated if an intramuscular wire is to be used for direct stimulation of the muscle.

When the skeletal muscle energy conversion system is to be used to power a circulatory assist device, a preferred muscle is the latissimus dorsi. The latissimus dorsi is capable of generating sufficient power to drive full cardiac output from a VAD if the energy is harnessed as proposed in the preferred embodiments of this invention. Other muscles may also be effective in a system such as this, but the preferred design uses the latissimus dorsi, which is left basically in situ, so that a normal preload stretch is allowed, and the muscle will pull in direct tension for maximal efficiency. There is minimal surgical dissection with little disruption of the neuro-vascular bundle, and blood supply collaterals are unaltered. The muscle insertion is surgically removed from the humerus and reattached to the skeletal muscle energy convertor which is firmly attached to the rib cage.

Use of the hydraulically-actuated system allows for considerable flexibility in locating components. From an engineering viewpoint, minimizing manipulation of the latissimus muscle is best realized with a hydraulically-actuated coupling between the muscle and blood pump(s). As discussed above, the energy convertor can be located in close proximity and in linear alignment with the latissimus dorsi, while the hydraulic actuator can be located in close proximity to the heart, with a small diameter hydraulic line connecting the two.

The body of the hydraulic convertor should be attached firmly, preferably to three ribs. This location requires a coupling length of only 2 to 4 cm between the preferred latissimus dorsi muscle and the movable part, e.g., piston shaft, of the energy converter. The distance that the point of attachment between the muscle and the convertor travels during contraction should be minimized to lessen the extent of scar tissue or encapsulation formation. Fluid dynamic considerations call for locating the two-stage hydraulic actuator (high-to-low pressure convertor) to be positioned as close to the blood pump as possible. In a preferred mode, the actuator is dome shaped so that it can be placed in the apex of the thoracic cavity where it will least affect lung function. By locating the hydraulic convertor outside the chest wall at the dome of the cavity over the first intercostal space, it can be directly coupled to a high-to-low pressure hydraulic actuator positioned directly inside the thoracic cavity. This provides three advantages: (1) It minimizes the length of tubing connecting the actuator and convertor. (2) Each component will stabilize the other, thus minimizing the forces on the attachment to the skeletal system. (3) The actuator can be located in close proximity to the major blood vessels and heart. Of course, positioning of the hydraulic convertor must allow for the travel of the piston as the muscle contracts. Therefore, the piston and cylinder may be curved to accommodate the curve of the rib cage as the piston follows the contracting muscle. In addition, provisions are also made for custom fitting certain lengths of the interconnecting cannulae. Those skilled in the art will recognize alternative muscles and attachment sites which may be used for the skeletal muscle energy conversion system, in accordance with the above teaching.

Attachment Procedures

The biologic to mechanic device interfaces are critical. There are two main interfaces—muscle attachment and fixation to the skeleton. The fixed part of the energy convertor, e.g., cylinder 144 of convertor 130, is firmly attached to the skeleton, and the muscle is inelastically connected to the fixed part of the convertor in order to transfer the energy expended by contraction of the muscle to the convertor.

The high pressure energy convertor must be rigidly fixed to the skeleton, preferably to the ribs, so that contraction of the muscle can provide displacement of the piston. This preferably will be achieved by attaching metal plates to 2 or 3 ribs, using techniques familiar to those skilled in the art. The energy convertor is then rigidly attached to these plates, as schematically illustrated in FIG. 2. The exact anatomic placement and shapes may be selected by the skilled worker, based on anatomic variation of the patients and needs of the actuator system.

The muscle must pull against a rigidly-fixed convertor body for maximum efficiency and transmission of its energy. Location of the convertor over the second and third ribs will provide stable fixation when the preferred latissimus dorsi muscle is used. In a preferred alternative, a plate can be fixed to the first three ribs and the convertor attached to this. Then, the actuator may be positioned on the inside of the thoracic wall just beneath the convertor. Closely coupling these two components will form a sandwich with the thoracic wall fixed between thus providing rigid fixation.

Means for attaching the muscle directly to the piston shaft, or other movable part, of the hydraulic convertor is required, after the muscle tendon is separated from the humerus. Bonding must occur in a relatively short time and, once established, last for years. The latissimus tendon may be used as the biologic interface between the muscle and the convertor piston shaft. This broad strong band of tissue attaches to the proximal humerus and can be easily separated. This tendon is avascular, as all tendons are, and it will not survive without a blood supply, nor will a healing process occur between the biologic and mechanical components. Transposition of a muscle flap from a second muscle may be used to promote healing, due to the vigorous blood supply of this tissue (see, e.g., Schwartz, et al., (1989), Principles of Surgery, 5th edition, McGraw Hill, New York, p. 2094).

Figure 37:
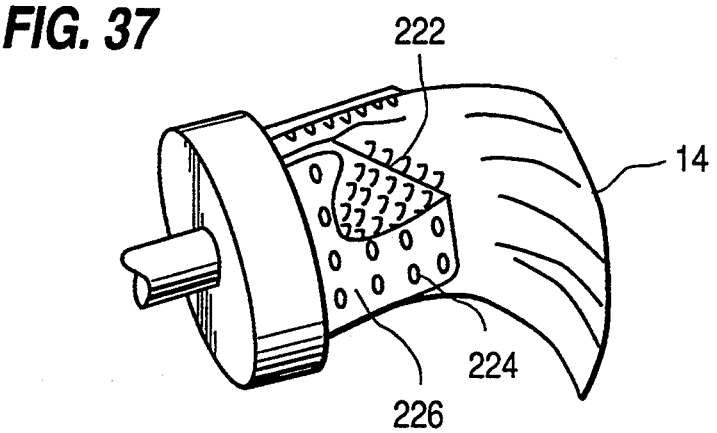
FIG. 37 is an illustration of the muscle attachment according to one embodiment of this invention.

Alternatively, the attachment could be performed directly to the belly of the muscle itself. This would allow for a broader attachment with better load distribution, and faster more secure adhesion to tissues containing an abundant blood supply. In one alternative, a fan-shaped piece of physiologically-comparable felt 226, preferably a Dacron TM felt, with a myriad of projecting hooks (similar to the hook-and-pile principle) is applied to each side of the muscle 14, as illustrated in FIG. 37. The hooks 222, augmented by several sutures 224 to ensure good aposition and contact would also help absorb the load postoperatively while the fibrous tissue formed between the felt 226 and muscle 14. An outer layer of smooth polyurethane coating on the backside of the felt will prevent adhesions from limiting movement. Preliminary in vivo implants of such material (according to U.S. Pat. No. 4,430,998, incorporated herein by reference) have demonstrated attachment within two weeks, during which time sutures were placed so that they carried the relatively light loads that would normally occur in training. These experiments demonstrated feasibility of this approach.

Figure 38:
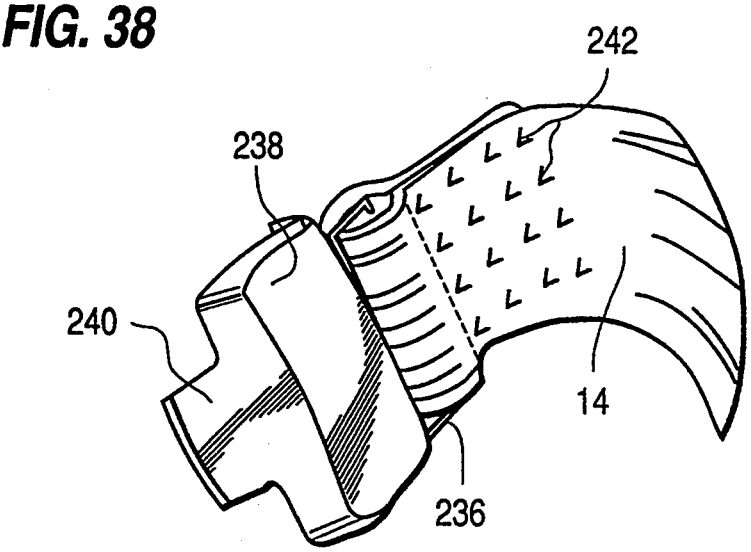
FIG. 38 is an illustration of the muscle attachment according to another embodiment of this invention.

A second alternative method of attachment, as shown in FIG. 38, contemplates a simple wrapping of the muscle 14 tendon or belly through an open loop 236 projecting from an end piece 238 of the piston shaft 240 and sewing the muscle or tendon to itself with sutures 242. In the embodiment shown, the open loop has a generally rectangular shape, however, other shapes are of course possible. This would eliminate the need for gripping devices puncturing the biologic tissue.

Figure 39:
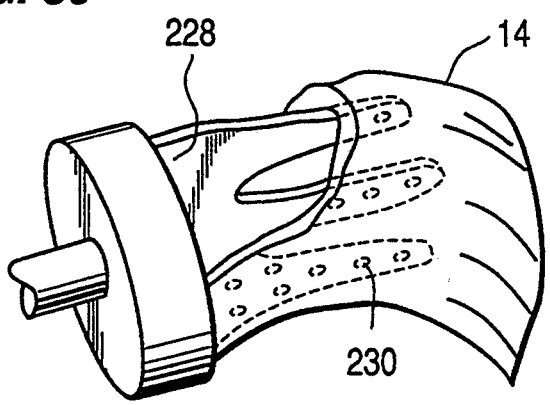
FIG. 39 is an illustration of the muscle attachment according to yet another embodiment of this invention.

More rapid tissue adhesion will occur when the blood supply is greatest; in muscle, the blood supply is greatest within the belly of the muscle itself. A third alternative, as shown in FIG. 39 provides a broad textured or lacy implant 228 sewn with sutures 230 into the muscle 14 itself which would heal in faster and more securely. This implant is preferably fabricated from a non-biodegradable material such as Dacron. Where it emerges from the muscle, it is optimally overcoated with smooth polyurethane to prevent adhesions from limiting movement.

Materials for the Implantable Devices

Materials for the muscle stimulator components are those typically used in implantable pacemakers and defibrillators. Preferred materials for the blood pumps and related "soft" components such as the grafts interconnecting the blood pumps to the major blood vessels are based on polyurethane, such as Biomer TM or polyurethaneurea material incorporating silicone additives on the surface as described in U.S. Pat. Nos. 4,675,361 and 4,689,383, incorporated herein by reference. The polyurethane with siliconized surface is particularly preferred. This biomaterial has excellent tissue compatibility, in vivo stability, and fatigue characteristics. This state-of-the-art biomaterial should also meet the requirements of the "soft" components of the myoplasty system. Parts in the hydraulic system and related "hard" category are preferably made of titanium. This material is extremely corrosion resistant, very strong, and relatively lightweight. Hydraulic fluid will preferably be isotonic saline or possibly silicone fluid. The primary consideration in the final selection will be to minimize transport across elastomeric interfaces such as the blood pumps due to osmotic pressure gradients.

Postoperative Care

Patients suffering from severe congestive heart failure are likely to need circulatory support from the time of implantation. The blood pumps are capable of being utilized immediately following implantation, and immediate and continuous operation of the pumps is desirable in order to maintain the patency of the blood pumps and support the patient's circulation. However, the skeletal muscle energy conversion subsystems require a quiescent period of healing-in, followed by a period of conditioning to convert the fast twitch, easily fatigued fibers of the skeletal muscle to fatigue-resistant slow twitch fibers.

The use of a hydraulic system affords a good solution to this dilemma. During surgery, the full system should be implanted with an external access port to permit access to the hydraulic system of the skeletal muscle energy conversion system. At the completion of surgery, the blood pumps are actuated by an external hydraulic pump connected through the external access port. During the postoperative heal-in period, this mode of operation may be used exclusively. The preferred external access port is similar to that described herein allowing external operation of the blood pump and simultaneous, independent monitoring of the energy conversion capability of the muscle during healing-in. But of course, any access port allowing temporary external operation of the blood pump is within the contemplation of this invention.

In the simplest form, the external access port will be connected by a 2-position, 3-way valve to the hydraulic system in a manner such that the blood pump is either operated by the external pump or by the skeletal muscle energy conversion system. The external hydraulic pump is preferably connected through a small diameter hydraulic line to the 3-way valve. This hydraulic line will usually include a percutaneous cuff, similar to that on VAD cannulae. With the simplest access port, the muscle will usually be in isometric contraction during conditioning, since the hydraulic convertor to which it is attached will be valved-off, and thus in an incompressible hydraulic filled state. With the preferred access port described herein, the hydraulic convertor is connected to an external monitor, providing a resistance which allows linear displacement during contraction of the muscle and monitoring of muscle conditioning progress. After the appropriate postoperative heal-in period and after conditioning the muscle (about three to tour weeks total time), the skeletal muscle can assume the pumping function. This is done by valving-off the external hydraulic pump, while simultaneously valving-in the skeletal muscle hydraulic conversion system.

The external hydraulic pump will preferably deliver 100 psi pressure fluid at from 30 ml to 60 ml per minute average flow. Peak flow rates will then be in the range of 90 to 200 ml per minute. These conditions can be met with a cam-driven metal bellows type pump, or simply a piston type pump. This pump needs to have a reliable life of up to several months, or about 10 million strokes, such as those generally available on the market. The hydraulic fluid would preferably be silicone oil, saline, or a physiologically equivalent fluid, that would not promote osmotic transport across a blood pump bladder.

When it is established that the skeletal muscle powered system is functioning smoothly, the percutaneous lead outward from the connection valve in the hydraulic line can be disconnected and explanted, and the wound closed and allowed to heal. The subcutaneous connection valve will preferably be left in place for use during; any future emergency in which the muscle was not able to provide the power to drive the blood pumps. It would be comforting to know that even in the event of an emergency need, there would be a back-up available if needed.

This approach eliminates the dilemma of the requirements of the early postoperative period for both circulating blood and for conditioning skeletal muscle, while also providing a means of alternate operation in the event of an emergency.

EXAMPLE 1

In Vitro Testing

An engineering model skeletal muscle VAD (MVAD) was fabricated for in vitro testing. Components were purchased off the shelf, and there was no attempt made for optimization of size and efficiency. The high pressure energy convertor was fabricated from a cylinder of 0.79 cm ID and a stroke length of 5 cm. The plunger of this piston was connected to a wire with a handle on the end for manual pulling, a form of skeletal muscle actuation. The cylinder was coupled hydraulically for test purposes with a smaller than optimum plastic tube of 3.2 mm outside diameter, 40 cm long. The second stage of the energy convertor was a second cylinder with a 1.1 cm ID and a 3.4 cm stroke connected to a pusher plate coupled to a modified clinical Thoratec TM Ventricular Assist Device with a stroke volume of 65 ml. This was connected to a mock circulatory loop containing a 0.9% saline solution with polyurethane cannulae 33 cm long and 16 mm interval diameter. Pulsatile VAD blood flow was measured with an electromagnetic blood flow probe in the VAD outflow cannula. Arterial and filling pressures were measured with Statham P23 pressure transducers, the high pressure was measured with an Ametek transducer, and displacement of the plunger in the first stage energy convertor was measured with a wire wrapped around a pulley connected to a potentiometer. All signals were digitized at 100 Mz with a Metrabyte analog to digital convertor connected to a personal computer and analyzed with software developed in the laboratory. Data was collected while pulling the handle manually at a rate of approximately 90 beats per minute.

Results

A recording showing the results of the initial MVAD in vitro test is presented in FIG. 42. During displacement of 4 to 5 cm, the pressure in the high pressure energy convertor reached 250 psi corresponding to applied forces of up to 9 kg, and an approximate stroke work of 4 joules per beat. VAD flow output averaged 5.2 L/min with a stroke volume of 58 ml and arterial pressure averaged 127/81 with a mean of 99 mmHg. The approximate VAD stroke work was about 0.9 joules.

EXAMPLE 2

Muscle Attachments

A fan-shaped piece of Dacron felt with a myriad of projecting ends or hooks (similar to the hook-and-pile principle) is applied to each side of the muscle (FIG. 37). The hooks, augmented by several sutures to ensure good aposition and contact also help absorb the load postoperatively while the fibrous tissue formed between the Dacron TM and muscle. An outer layer of smooth polyurethane coating on the backside of the felt prevents adhesions from limiting movement. Preliminary in vivo implants of Velcro TM -like material have demonstrated attachment within two weeks, during which time the sutures were placed so that they carried the relatively light loads that would normally occur in training. In these preliminary tests, a force of 2 kg was required to peel the material away from the caprine latissimus dorsi attached as described above. The hooks in the material used in these tests were known to be short for optimum fixation. In spite of these limitations, these experiments demonstrated initial feasibility of this approach to provide the secure attachment required.

It will be obvious to one of ordinary skill in the art that numerous modifications may be made without departing from the true spirit and scope of the invention which is to be limited only by the appended claims.

What is claimed is:

1. A dual access port comprising:
   a housing having a generally cubical body with a cylindrical recess in one side;
   a plurality of housing fluid passages within said housing;
   a housing end cap disposed over an upper surface of said housing and having a plurality of housing ports, each of said housing ports communicating with one of said plurality of housing fluid passages, respectively;

a rotatable cylinder disposed within said recess in said housing, said cylinder having an internal planar surface adjacent said recess and an external planar surface generally coplanar with an exterior surface of said housing;

a plurality of first cylinder fluid passages forming an internal passageway within said cylinder such that fluid both enters and exits said cylinder on the side of said external planar surface;

a plurality of second cylinder fluid passages passing through said cylinder;

a cylinder end cap disposed over said external planar surface of said cylinder in said recess, said cylinder end cap having a plurality of cylinder ports, each of said cylinder ports communicating with one of said plurality of first and second cylinder fluid passages, respectively; and rotation means for rotating said cylinder between at least a first position and a second position;

wherein rotation of said cylinder to said first position places at least one of said cylinder ports in communication with one of said first cylinder fluid passages such that fluid entering said at least one cylinder port exists another of said plurality of cylinder ports; and wherein rotation of said cylinder to said second position places at least one of said cylinder ports in communication with one of said second cylinder fluid passages, and said one of said second cylinder fluid passages is in communication with one of said housing fluid passages such that fluid entering said at least one cylinder port exits one of said housing ports.

2. The dual access port of claim 1 wherein said housing fluid passages extend from an external surface of said housing to said cylindrical recess.

3. The dual access port of claim 2 wherein said housing fluid passages make an approximately 90° bend between said upper surface of said housing and said cylindrical recess.

4. The dual access port of claim 1 wherein said first cylinder fluid passages include a plurality of 90° bends.

5. The dual access port of claim 1 wherein said rotation means comprises a side arm post connected to said cylinder and extending upwards through said housing and a groove in said housing allowing the movement of said post between said first position and said second position.

6. The dual access port of claim 1 wherein said housing cap including said housing ports is removable.

7. The dual access port of claim 6 wherein when said housing cap is removed, said access port further includes a sealing cap disposed over the openings of said housing fluid passages to thereby seal off said passages.

8. The dual access port of claim 1 further comprising a retainer ring disposed around said housing cap securing said cap to said housing.

9. The dual access port of claim 1 wherein said housing further comprises an O-ring seal between said upper surface of said housing and said housing cap such that leakage from said housing fluid passages is thereby prevented.

10. An access port adapted to be used in a hydraulic muscle energy conversion system including a high pressure hydraulic transmission line between a muscle energy conversion means and an implantable medical device and an alternate source of hydraulic power; said access port comprising:

an access port housing having a cylindrical recess;

at least one housing fluid passage in said housing;

a rotatable cylinder disposed within said recess in said housing;

at least one cylinder fluid passage in said cylinder;

rotation means for rotating said cylinder between a first position and a second position;

wherein said access port housing is adapted to be disposed in the high pressure hydraulic transmission line between the conversion means and the implantable medical device such that rotation of said cylinder to said first position allows fluid communication between the energy conversion means and the implantable medical device and rotation of said cylinder to said second position blocks fluid communication between the energy conversion means and the implantable medical device while allowing fluid communication between the implantable medical and the alternate source of hydraulic power.

11. The access port of claim 10 wherein said housing further comprises a removable housing end cap including at least one housing port, said at least one housing port being aligned with said at least one housing passage.

12. The access port of claim 11 wherein said housing further comprises a cylinder end cap including at least one cylinder port, said at least one cylinder port being aligned with said at least one cylinder fluid passage in said cylinder.

13. The access port of claim 12 wherein said at least one cylinder fluid passage includes at least one first cylinder fluid passage and at least one second cylinder fluid passage.

14. The access port of claim 13 wherein rotation of said cylinder to said first position aligns said at least one cylinder port with said at least one first cylinder fluid passage and rotation of said cylinder to said second position aligns said at least one cylinder port with said at least one second cylinder fluid passage.

15. The access port of claim 14 further including another said at least one cylinder port wherein said at least one first cylinder fluid passage includes a first opening aligned with said at least one cylinder port, a second opening aligned with another said at least one cylinder port, and an internal passageway within said cylinder thereby allowing fluid communication between said at least one cylinder port and said another cylinder port when said cylinder is in said first position.

16. The access port of claim 14 wherein said at least one second cylinder fluid passage includes a first opening aligned with said at least one cylinder port, a second opening aligned with said at least one housing fluid passage, and an internal passageway therebetween thereby allowing fluid communication between said at least one cylinder port and said at least one housing port when said cylinder is in said second position.

17. The access port of claim 11 wherein when said removable housing end cap including at least one housing port is removed, a housing sealing cap is disposed over said housing such that said at least one housing fluid passage is thereby sealed from an external environment.

18. A dual access port for use in an implantable hydraulic muscle energy conversion system including a high pressure hydraulic convertor connected to a muscle, a two-stage hydraulic actuator for transforming high pressure hydraulic energy into low pressure hydraulic energy which operates an implantable medical device, and a high pressure hydraulic transmission line interconnecting the convertor and actuator, said dual access port comprising:

a housing having a generally cubical body with a cylindrical recess in one side, said housing being disposed in the high pressure hydraulic transmission line and having means adapted to connect said housing between the convertor and the activator;

a plurality of housing fluid passages within said housing;

a housing end cap disposed over an upper surface of said housing and having a plurality of housing ports, each of said housing ports communicating with one of said plurality of housing fluid passages;

a rotatable cylinder disposed within said recess in said housing, said cylinder having an internal planar surface adjacent said recess and an external planar surface generally coplanar with an exterior surface of said housing;

a plurality of first cylinder fluid passages forming an internal passageway within said cylinder such that fluid both enters and exits said cylinder on the side of said eternal planar surface;

a plurality of second cylinder fluid passages passing through said cylinder;

a cylinder end cap disposed over said external planar surface of said cylinder in said recess, said cylinder end cap having a plurality of cylinder ports, each of said cylinder ports communicating with one of said plurality of first and second cylinder fluid passages; and rotation means for rotating said cylinder between at least a first position and a second position;

wherein rotation of said cylinder to said first position places at least one of said cylinder ports in communication with one of said first cylinder fluid passages such that fluid entering said at least one cylinder port exits another of said plurality of cylinder ports; and wherein rotation of said cylinder to said second position places at least one of said cylinder ports in communication with one of said second cylinder fluid passages, and said one of said second cylinder fluid passages is in communication with one of said housing fluid passages such that fluid entering said at least one cylinder port exits one of said housing ports.

19. The dual access port of claim 18 further comprising a percutaneous cuff to which said plurality of housing ports are connected by small diameter hydraulic lines.

20. The dual access port of claim 19 wherein said percutaneous cuff connects said housing ports to an external source of hydraulic energy.

21. The dual access port of claim 20 further comprising at least a first cylinder port of said plurality of cylinder ports which is connected to the hydraulic convertor by a first end of the high pressure hydraulic transmission line and at least a second cylinder port of said plurality of cylinder ports which is connected to the two-stage hydraulic actuator by a second end of the high pressure hydraulic line.

22. (amended) The dual access port of claim 21 further comprising an internal passageway between said first and second cylinder ports when said cylinder ports are connected by one of said first cylinder fluid passages and said cylinder is in said first position.

23. The dual access port of claim 21 wherein said second cylinder port is connected to one of said second cylinder fluid passages which is aligned with one of said plurality of housing fluid passages such that said second cylinder port connected to the actuator is in fluid communication with the external source of hydraulic energy through said percutaneous cuff, when said cylinder is in said second position.

24. The dual access port of claim 21 wherein further comprising an external monitoring device to which said percutaneous cuff is connected by said housing ports.

25. The dual access port of claim 24 wherein said first cylinder port is connected to one of said second cylinder fluid passages which is aligned with one of said plurality of housing fluid passages such that said first cylinder port connected to the convertor is in fluid communication with the external monitoring device through said percutaneous cuff, when said cylinder is in said second position.

* * * * *